United States Patent
Li et al.

(10) Patent No.: US 9,872,752 B2
(45) Date of Patent: Jan. 23, 2018

(54) MEDICAL ASSEMBLY AND A DEVICE FOR PLACEMENT OF THE MEDICAL ASSEMBLY

(71) Applicant: Boston Scientific Scimed, Inc., Maple Grove, MN (US)

(72) Inventors: Jamie Li, Lexington, MA (US); Timothy P. Harrah, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 139 days.

(21) Appl. No.: 14/201,301

(22) Filed: Mar. 7, 2014

(65) Prior Publication Data
US 2014/0257030 A1    Sep. 11, 2014

Related U.S. Application Data

(60) Provisional application No. 61/776,406, filed on Mar. 11, 2013.

(51) Int. Cl.
*A61F 2/00* (2006.01)

(52) U.S. Cl.
CPC .......... *A61F 2/0063* (2013.01); *A61F 2/0045* (2013.01)

(58) Field of Classification Search
CPC .. A61F 2/0046; A61F 2/0063; A61B 17/0469; A61B 17/00491; A61B 2017/00805; A61B 2017/0409; A61B 2017/0472
USPC .................................................. 600/29–32, 37
See application file for complete search history.

(56) References Cited

U.S. PATENT DOCUMENTS

| | | | |
|---|---|---|---|
| 2006/0122457 A1* | 6/2006 | Kovac | A61F 2/0036 600/37 |
| 2010/0174134 A1* | 7/2010 | Anderson | A61B 17/06109 600/37 |
| 2010/0305394 A1* | 12/2010 | Rosenblatt | A61F 2/0063 600/30 |
| 2011/0098527 A1 | 4/2011 | Goldberg | |
| 2012/0108894 A1* | 5/2012 | Young | A61F 2/0045 600/37 |
| 2013/0012768 A1* | 1/2013 | Koullick | A61L 31/06 600/37 |

* cited by examiner

*Primary Examiner* — Samuel Gilbert
(74) *Attorney, Agent, or Firm* — Brake Hughes Bellermann LLP

(57) ABSTRACT

According to an aspect, a medical assembly includes a ring shaped member configured to surround a vaginal wall and an arm member. The arm member is coupled to the ring shaped member and configured to extend from the ring shaped member to a bodily location. The arm member is configured to be coupled to the bodily location and provide a support to a vagina of a patient. The ring shaped member is configured to hold the arm member during implantation of the arm member within the body. The ring shaped member is further configured to be cut after implantation so that the ring shaped member is transformed into a non-circular shape.

10 Claims, 20 Drawing Sheets

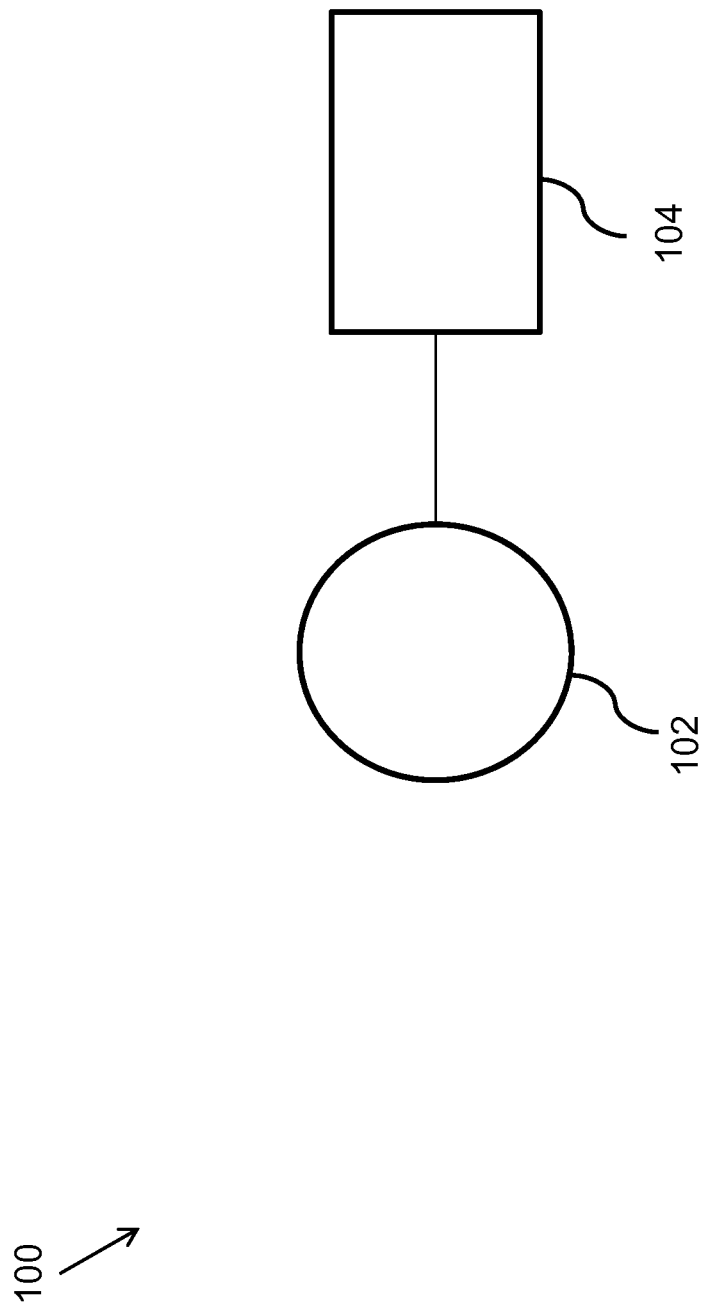

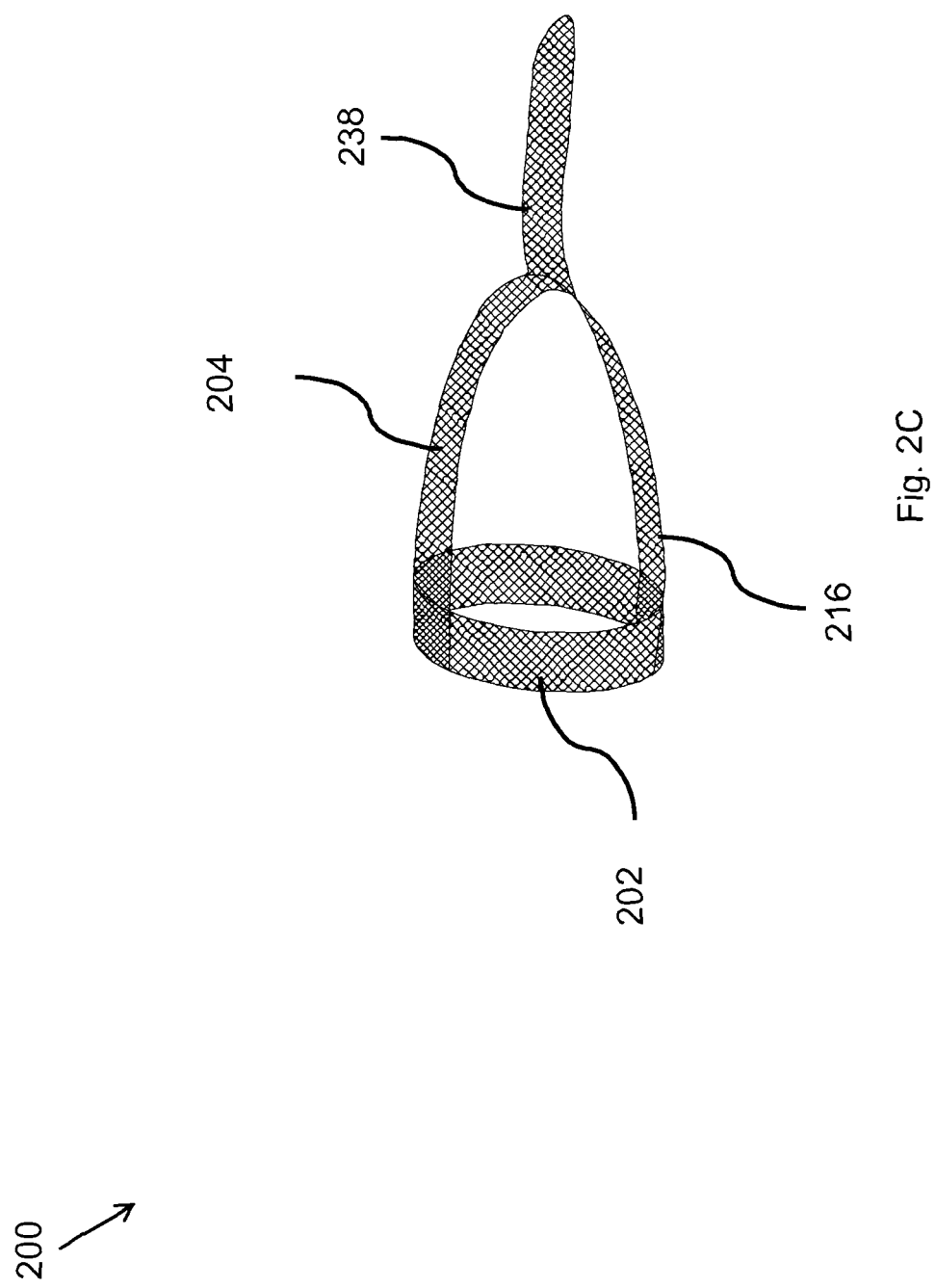

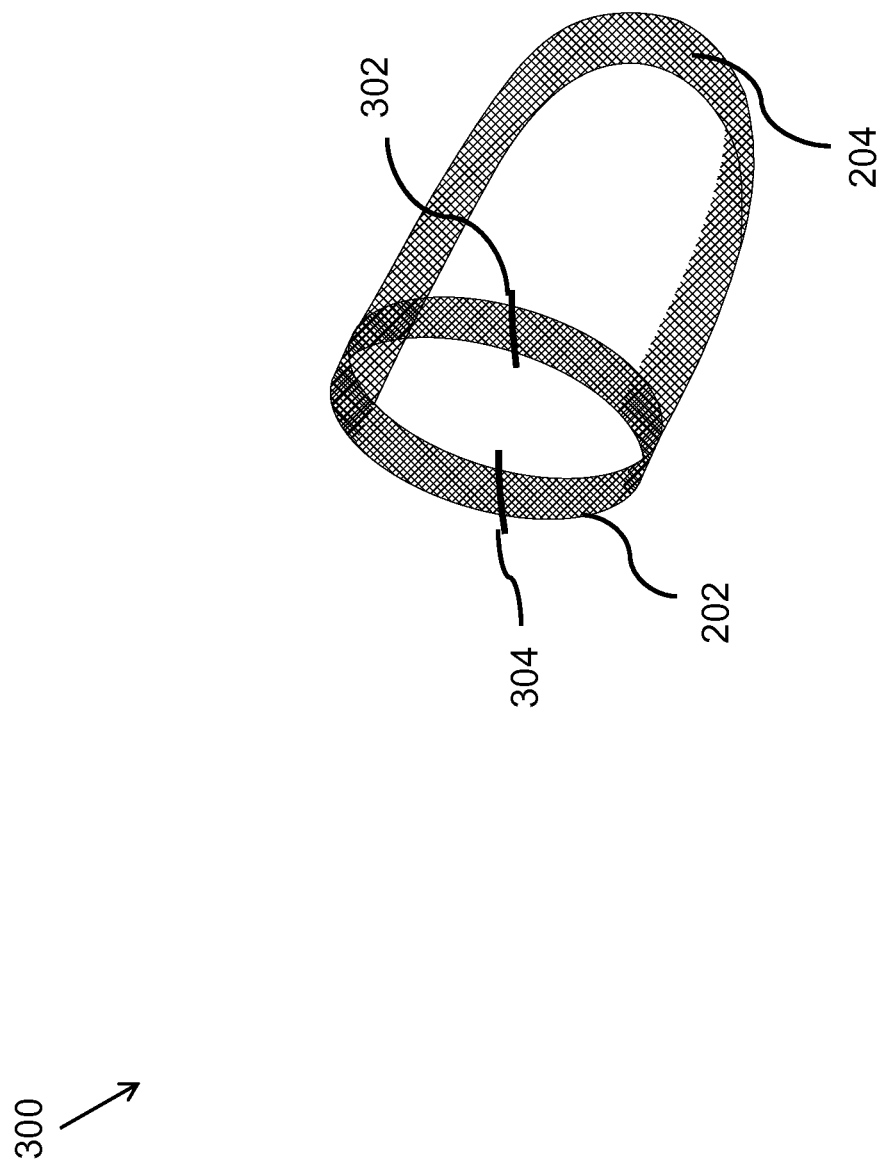

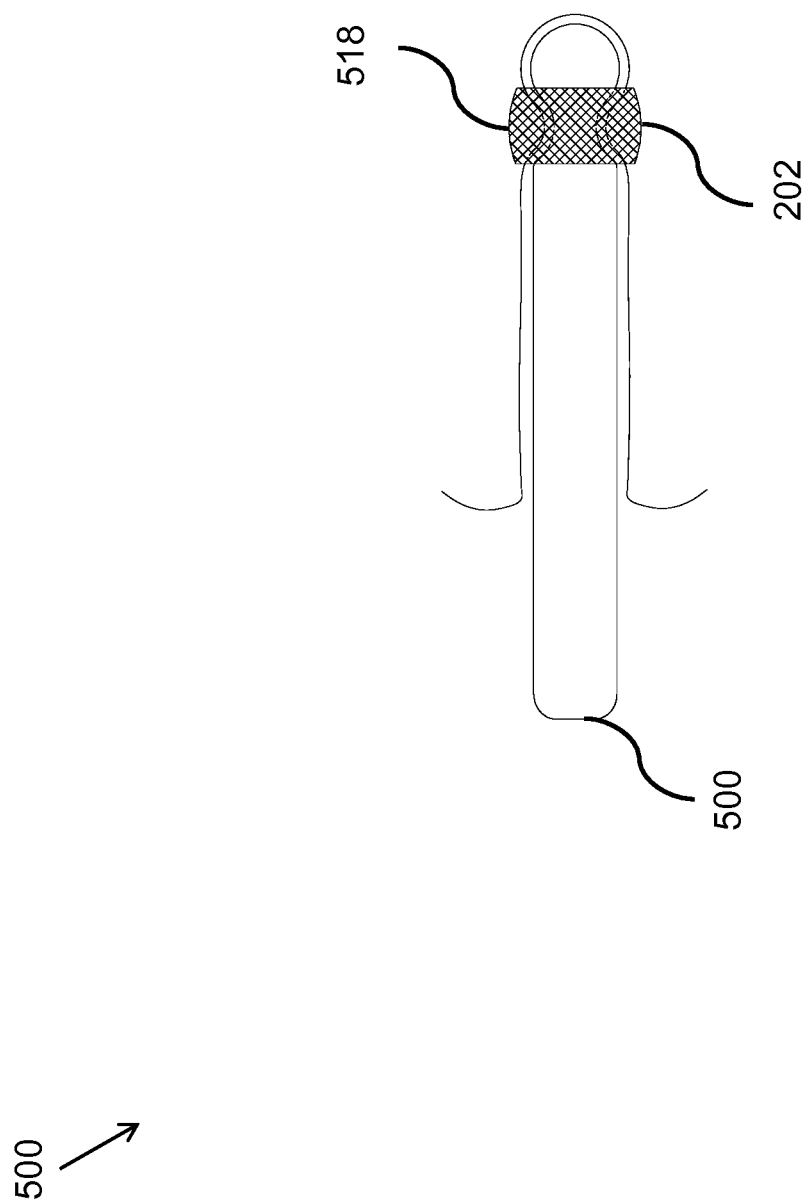

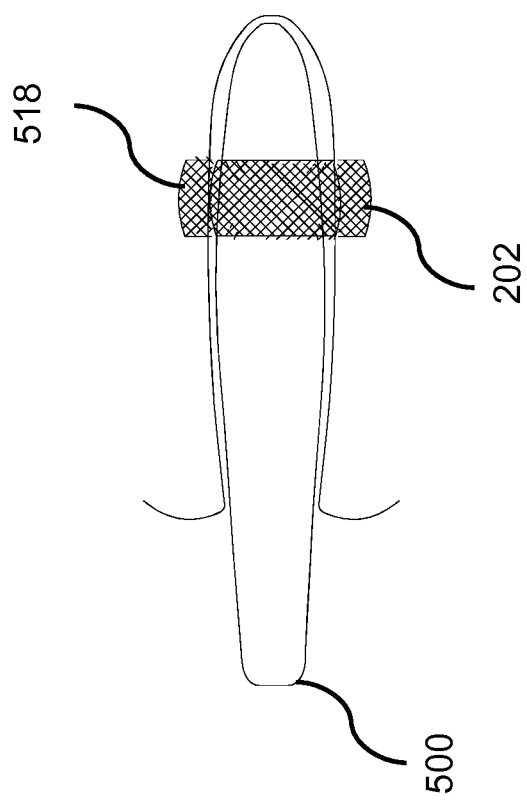

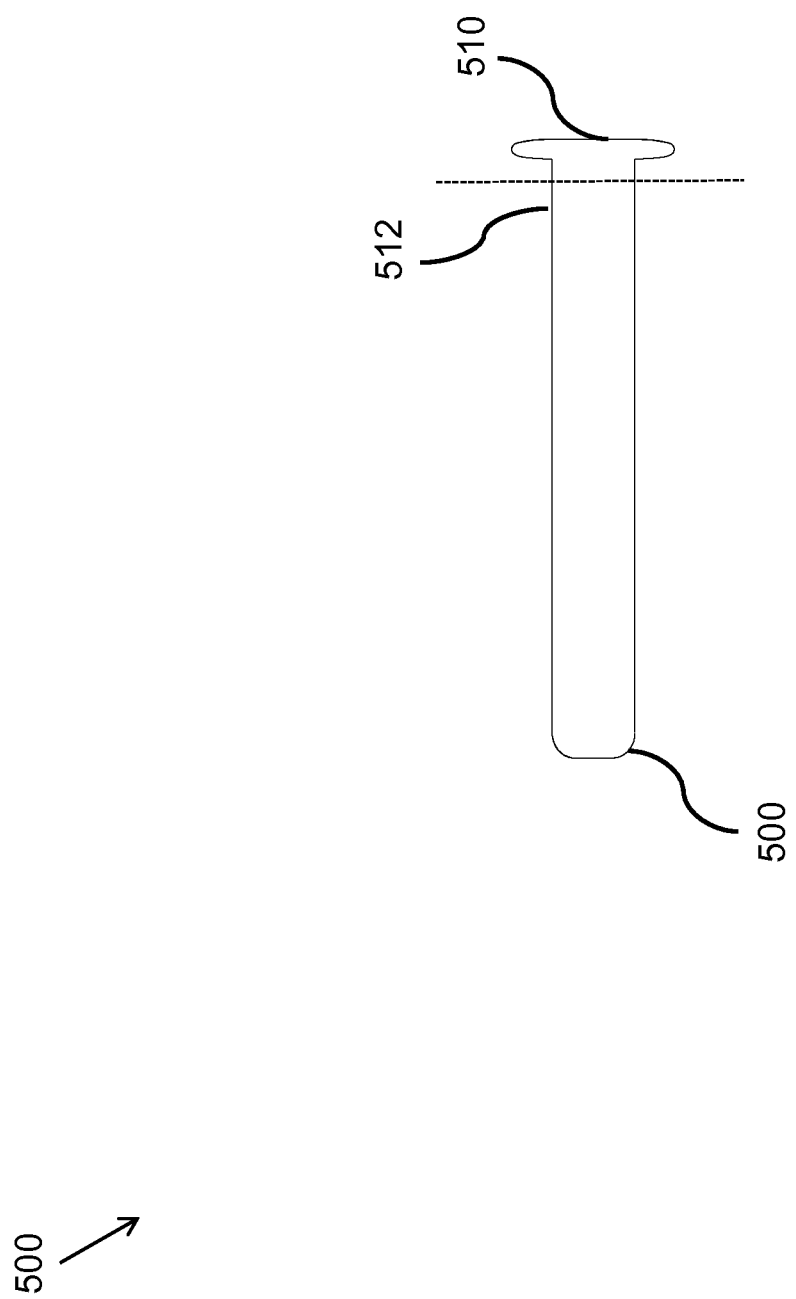

MEDICAL ASSEMBLY AND A DEVICE FOR PLACEMENT OF THE MEDICAL ASSEMBLY

CROSS REFERENCE TO RELATED APPLICATION

This application is a Nonprovisional of, and claims priority to, U.S. Patent Application No. 61/776,406, filed on Mar. 11, 2013, entitled "MEDICAL ASSEMBLY AND A DEVICE FOR PLACEMENT OF THE MEDICAL ASSEMBLY", which is incorporated by reference herein in its entirety.

FIELD

The present invention generally relates to implants and more particularly to bodily implants and their delivery and placement into a patient's body for the treatment of pelvic floor disorders.

DESCRIPTION OF THE RELATED ART

A pelvic floor disorder occurs when one or more pelvic muscle or connective tissue in the pelvic region weakens or are injured. Some of the cases may be as a result of damages to vaginal or pelvic support tissue by stretching or tearing of the connective tissue within a pelvic space due to childbirth, age, obesity, post-menopausal conditions or chronically elevated intra-abdominal pressure, pelvic surgery, or radiation treatments. There are a variety of problems related to the pelvic floor such as pelvic organ prolapse such as vaginal prolapse, urinary incontinence, and anal incontinence.

Treatment of these problems can be accomplished through pelvic floor rehabilitation, dietary changes, or surgical procedures. One of the surgical treatments includes a sling procedure involving placing an implant such as a sling into a patient's body around the vagina.

Surgical treatments may include various surgical devices and procedures that focus on supporting a portion of the vagina by using a bodily implant. The implant is configured to surround a portion of the vagina and provide support to the vagina in order to restore native anatomy and function. In many instances the bodily implant is a mesh implant or includes a mesh.

The implant usually lacks a definite structure and is therefore quite tedious to handle during an implantation procedure. Also, the implant is substantially flexible in nature thereby leaving a scope for undesirable movement in and around the region where the implantation procedure is to be carried out.

Therefore, in light of the above, there is a need to find a suitable way to prevent the undesirable mesh movement and rendering the mesh more amiable to implantation.

SUMMARY

In an embodiment, the invention discloses a medical assembly comprising a ring shaped member configured to surround a vaginal wall and an arm member. The arm member is coupled to the ring shaped member and configured to extend from the ring shaped member to a bodily location. The arm member is configured to be coupled to the bodily location and provide a support to a vagina of a patient. The ring shaped member is configured to hold the arm member during implantation of the arm member within the body. The ring shaped member is further configured to be either cut after implantation or to partially biodegrade so that the ring shaped member is transformed into a non-circular shape immediately or shortly after implantation. Accordingly, in some embodiments, a medical practitioner may cut the ring shaped member and in other embodiments, the ring shaped member may biodegrade to loosen.

In an embodiment, the invention discloses a medical device comprising an elongate portion configured to be inserted into a vagina and a head portion. The elongate portion has a proximal end portion and a distal end portion. The head portion extends from the distal end portion of the elongate portion. The head portion includes a tip portion and a shoulder. The shoulder defines a diameter different than a diameter defined by the elongate portion and the tip portion such that the shoulder is configured to hold an implant portion disposed around a vaginal wall.

In an embodiment, the invention discloses a method comprising placing a medical assembly within a body of a patient such that a ring shaped member of the medical assembly surrounds an outer surface of a vaginal wall of the patient. The method further includes securing an arm member of the medical assembly to the vaginal wall. The arm member extends from the ring shaped member to a body location. The arm member is configured to support the vagina of the patient, wherein the ring shaped member is configured to temporarily hold a portion of the arm member stationary with respect to a portion of the vagina during securing;

BRIEF DESCRIPTION OF THE FIGURES

The invention and the following detailed description of certain embodiments thereof may be understood by reference to the following figures:

FIG. 1 is a schematic diagram of a medical assembly configured to be delivered into a patient's body for the treatment of pelvic floor disorder, in accordance with an embodiment of the present invention.

FIG. 2C is a perspective illustration of a medical assembly configured to be delivered into a patient's body for the treatment of pelvic floor disorder.

FIGS. 3A-3C illustrate medical assemblies in accordance with some embodiments of the invention.

FIG. 5B illustrates a perspective view of the medical device of FIG. 5A placed into the body of the patient to provide support to the medical assembly.

FIG. 5D illustrates a perspective view of the medical device of FIG. 5C being placed into the body of the patient.

FIG. 5E illustrates a perspective view of a medical device configured to be placed into a body of a patient to provide support to a medical assembly.

DETAILED DESCRIPTION

Figure 2A:
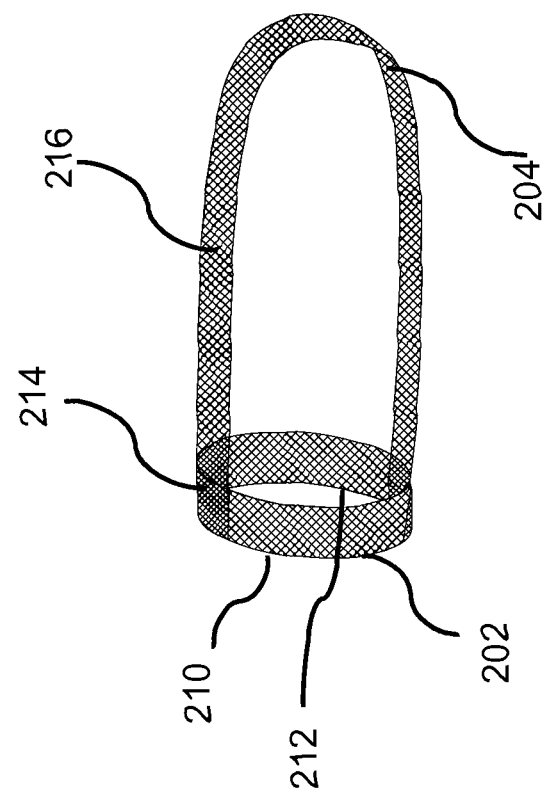
FIG. 2A is a perspective illustration of a medical assembly configured to be delivered into a patient's body for the treatment of pelvic floor disorder.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The present invention relates to bodily implants and methods for their delivery and placement into a patient's body for the treatment of pelvic floor disorders such as pelvic organ prolapse, urinary incontinence, anal incontinence, and the like. In some embodiments, the bodily implants act as vaginal supports and facilitate in proper tensioning of pelvic muscles surrounding the vagina to prevent pelvic floor disorder. In some embodiments, the vaginal support provided by the bodily implants involves formation of a loop around the vagina and thereby aiding in fixation into a patient's body during pelvic floor repair. In some embodiments, this loop structure applies a tensioning force to maintain the vagina of a patient in a position that is more desired for preventing pelvic floor disorders. In some other embodiments, the bodily implants of the present invention can be used to support bodily locations or organs other than the vagina.

The term patient may be used for a person who is benefitted of the bodily implants and/or other devices and/or the surgical procedures of the present invention. For example, the patient can be a person within whom the bodily implant is delivered and placed. The patient may be a human female, a human male or any other mammal.

The terms proximal and distal described in relation to various devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like who may perform the procedure of delivery and placement of the bodily implants into the patient's body as described in the present invention. The term proximal refers to an area that is closest to the operator. The term distal refers to an area that is farthest from the operator.

FIG. 1 is a schematic diagram of a medical assembly 100 configured to be delivered into a patient's body for the treatment of pelvic floor disorders, in accordance with an embodiment of the present invention. The medical assembly 100 includes a ring shaped member 102 and an arm member 104.

The ring shaped member 102 is configured to surround a bodily portion. For example, in some embodiments, the ring shaped member 102 is configured to surround or substantially surround a vaginal wall. In other embodiments, the ring shaped member 102 is configured to surround or substantially surround a different portion of the body, such as a uterus, a rectum, or other bodily portion. In some embodiments, the ring shaped member 102 is structured in a manner such that it is configured to completely surround the vagina or vaginal wall. In some embodiments, the ring shaped member is a complete ring. In other embodiments, the member is C shape or does otherwise not form a complete ring. In some embodiments, the ring shaped member 102 is configured to provide a support to a vagina of the patient during an implantation procedure of a bodily implant (for example a mesh) into the pelvic region of the patient.

In some embodiments, the ring shaped member 102 can further be configured to be cut or released after implantation so that the ring shaped member 102 is transformed into a non-circular shape or substantially non-circular shape such as a linear shape or any other shape, and thereby reducing a risk of constriction of the vagina. In some embodiments, a portion such as an unneeded portion of the ring shaped member can also be removed by cutting or releasing it from the medical assembly. Additionally, in some embodiments, sutures or fasteners may be cut or removed to allow the ring shaped member 102 to transform in shape. In some embodiments, the sutures or fasteners maybe biodegradable. In other words, in some embodiments, the sutures or fasteners may dissolve over a period of time in the body to allow the ring shaped member to transform in size and/or shape.

In some embodiments, the ring shaped member 102 is manufactured as a single component having a ring shape. In some embodiments, the ring shaped member 102 is manufactured as a multi component system, which is coupled to form the ring shaped member 102. The multi-component system can include a first component portion and a second component portion (not shown). The first component portion can be configured to be coupled to the second component portion such that the ring shaped member 102 is formed. The second (or additional) component portion(s) can be biodegradable and/or include an elastic portion to facilitate the implantation process. In some embodiments, the multi component system includes more than two component portions that can be coupled to form the ring shaped structure 102.

The ring shaped member 102 can be of a variety of different shapes, sizes, and configurations depending on the intended use of the medical assembly 100 and location of its placement within the body of the patient. The ring shaped member 102 can be shaped and sized to support the portion of the vagina of the patient. In accordance with some embodiments, the ring shaped member 102 may be configured to conform to the shape of an organ or a tissue of the body of the patient. For example, the ring shaped member 102 may be placed in a ring shape, such as in the shape of a vaginal ring, to help it conform to the external contour of vagina for easier fixation. In some embodiments, the ring shaped member may not be a perfect ring before placement and delivery around the vaginal wall. For example, the ring shaped member can be a simple cyclic structure in the form of a loop such as its one end portion is attached to the second end portion (in cases of multi component system) or it does not have any end portion (in cases of a single component system). In such embodiments, the ring shaped member is configured to conform and adapt to a shape of a ring or any other circular or non-circular shape when placed on or around a bodily tissue. In some embodiments, the ring shaped member 102 can conform to a shape such as substantially rectangular, square, oval, or elliptical, and the like. Ring shaped member 102 may encircle the tissue in a plane that is substantially perpendicular to the longitudinal axis of the tissue or member 102 may encircle the tissue in a plane that is at an angle with respect to the longitudinal axis.

The ring shaped member 102 can be designed to have a coupling site. In some embodiments, the ring shaped member 102 has one coupling site. In other embodiments, the number of coupling sites is more than one. The coupling site is the portion of the ring shaped member 102 which is used for coupling the ring shaped member 102 to the arm member. The coupling site, for example, may have some coupling arrangement such as a glue etc. that can be used for coupling the arm member at the coupling site.

In some embodiments, the coupling site can be designed to temporarily couple the arm member 104 (as discussed below) to the ring shaped member 102. In other embodiments the coupling site is designed to permanently couple the arm member 104 to the ring shaped member 102.

In some embodiments, the ring shaped member 102 can be designed such that the entire surface of the ring shaped member 102 can be used to couple the arm member 104 to the ring shaped member 102.

In some embodiments, the arm member 104 is configured to be coupled to the ring shaped member 102 at the coupling site and is configured to extend from the ring shaped member 102 to a bodily location upon placement. For example, the length of the arm member 104 can be provided to be configured to extend to the body location. In some embodiments, the length of the arm member 104 elastic or stretchable and may thus be adjustable. The ring shaped member 102 can be configured to provide a uniform grip and support to the arm member 104 thereby aiding in better fixation of the arm member 104.

In some embodiments, the arm member 104 is removably or fixedly coupled to the ring shaped member 102. In some embodiments, the arm member 104 is integrated to the ring shaped member 102 such that the ring shaped member 102 and the arm member 104 form a single integral structure.

In certain embodiments, the arm member 104 can be configured to be held by the ring shaped member 102 during implantation of the arm member 104 within the body. In some embodiments, the arm member 104 is coupled to the ring shaped member 102 at the coupling site of the ring shaped member 102.

A portion of the arm member 104 is configured to be coupled to the bodily location and provide a support to a vagina of a patient. For example, in an embodiment, a portion of the arm member 104 is configured to extend to a sacrum of a patient. In some embodiments, the arm member 104 extends from the ring shaped member 102 to a location posterior to the vagina of the patient. In other embodiments, the arm member 104 extends from the ring shaped member 102 to a location anterior to the vagina of the patient.

In embodiments, the arm member 104 can contain one or more arms. For example, in some embodiments, the arm member 104 can contain a single arm. In some embodiments, the arm member 104 can contain multiple arms. In an example, the arm member can have a single arm referred to as a first arm such that the first arm is configured to extend from the ring shaped member to a bodily location. In such cases, the arm member can have a shape such as a U-shape. In an example, the arm member can have two arms—the first arm and a second arm such that the first arm is configured to extend from the ring shaped member and couple to the second arm and the second arm is configured to extend from the first arm to a bodily location. In such cases, the arm member can have a shape for example a yoke shape. The bodily location can be a location posterior or anterior to the vagina of the patient, a sacrum or tissues proximate to the sacrum, or any other body location. In some embodiments, the bodily location can be one of the bones or tissues at or proximate the back of the pelvis. In some embodiments, the bodily location can be a hip bone. In some embodiments, the bodily location can be a coccyx. In some embodiments, the bodily location can be a sacrospinous ligament or any other body location. In some other embodiments, a third, fourth or even more arms can also be provided.

In some embodiments, the medical assembly 100 may be or include a mesh based device. For example, in some embodiments, the mesh can have a specified weight. In some embodiments, the mesh weight can be approximately between 15 g/cm$^2$ to 35 g/cm$^2$ (e.g., 20 g/cm$^2$, 25 g/cm$^2$, 30 g/cm$^2$). In other embodiments, the mesh weigh may be greater than 35 g/cm$^2$. In some embodiments, the medical device 100 may be a sling system that can be utilized in the treatment of pelvic organ disorders. In some embodiments, the medical assembly 100 or a portion of the medical assembly 100 such as the ring shaped member 102 and/or the arm member 104 can be formed of a material that allows tissue in-growth after implantation. In an embodiment, the ring shaped member 102 and/or the arm member 104 can be made from a biological material or a cadaveric tissue. In another embodiment, the ring shaped member 102 and/or the arm member 104 may be made up of synthetic material or natural materials such as plastic, polypropylene mesh or other plastic materials, stem cells, natural xenograft material, collagen growth factors, and the like. In some embodiments, the synthetic material may be elastic and flexible, which may allow stretching of the medical assembly 100 without abdominal straining. In some embodiments, the ring shaped member 102 and/or the arm member 104 are made of flexible material. In other embodiments, the ring shaped member 102 and/or the arm member 104 are made of elastic material. Additionally, the medical assembly 100 may be coated, impregnated, or formed with one or more drugs to be eluted to an adjacent tissue, in accordance with several embodiments.

In some embodiments, the arm member 104 may have a varying width. For example, in some embodiments, the arm member 104 maybe wider at the mid-portion or the portion that is configured to contact and provide support to the vagina. Additionally in some embodiments, the end portions of the arm member 104 may include a larger width. In such embodiments, the larger width may help facilitate the anchoring or coupling of the arm member 104 to bodily tissue.

In some embodiments, the ring shaped member 102 and the arm member 104 are formed of the same material. In certain embodiments, the ring shaped member 102 and the arm member 104 are formed of different materials. For example, the ring shaped member 102 can be formed from a first material and the arm member 104 can be formed from a second material different than the first material. In some embodiments, the arm member 104 is elastic and is configured to stretch.

The arm member 104 can have a variety of sizes (length, width, and thickness) depending on the intended use of a particular medical assembly such as the medical assembly 100 and the intended site of implantation. For example, the size of the arm member 104 can have a length such that the ring shaped member 102 can be placed through and secured to surrounding bodily tissues.

FIG. 2A is a perspective illustration of a medical assembly 200 configured to be delivered into a patient's body for the treatment of pelvic floor disorders, in accordance with an embodiment of the present invention. The medical assembly 200 includes a ring shaped member 202 and an arm member 204.

Figure 2B:
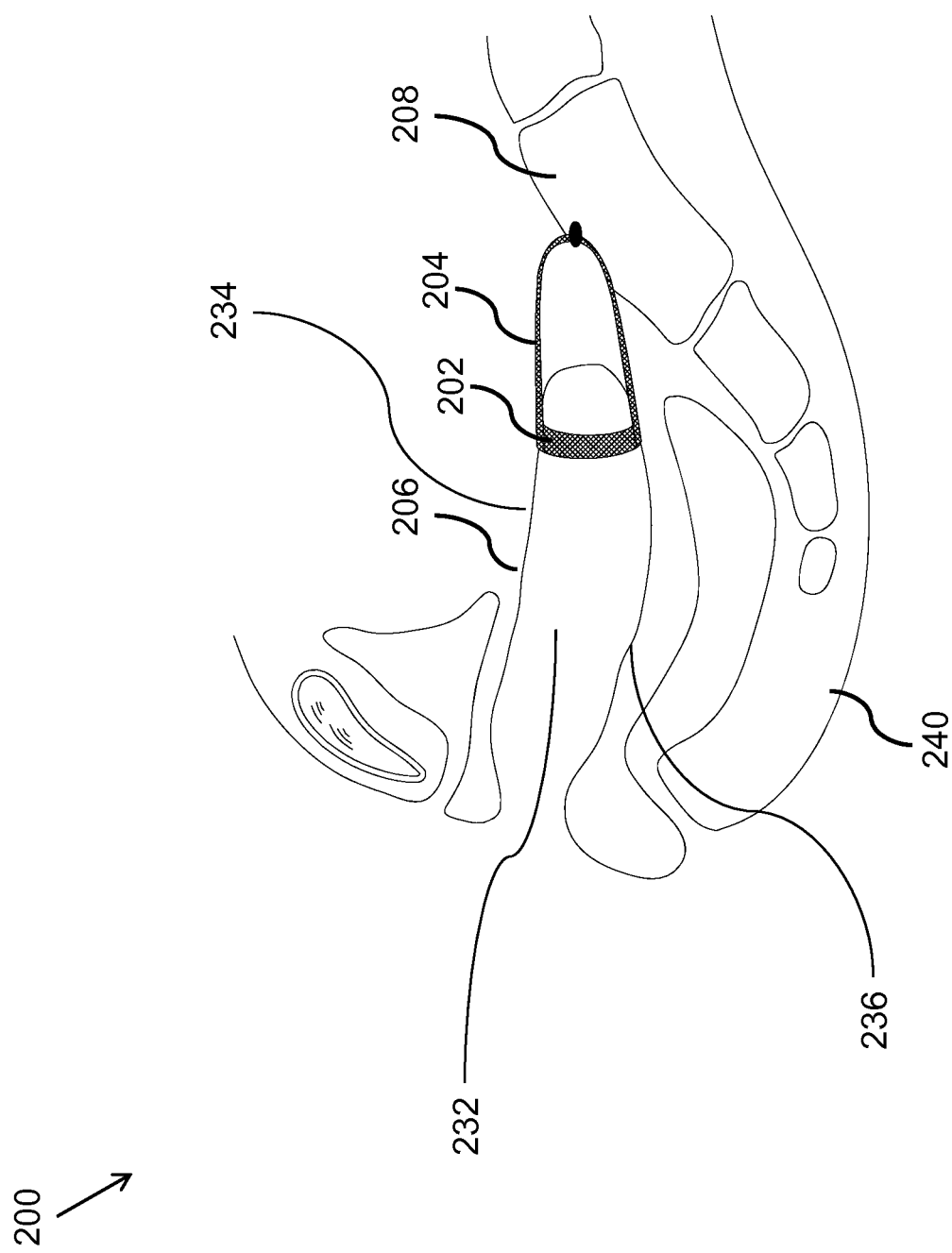
FIG. 2B is an illustration of placement of the medical assembly of FIG. 2A inside the body of the patient.

The ring shaped member 202 is configured to surround an outer vaginal wall 206 (also referred to as the outer wall 206 of the vagina), as illustrated in FIG. 2B. Referring now to FIGS. 2A and 2B, in an embodiment, the ring shaped member 202 is configured to completely surround (i.e., form a complete loop or ring around) a portion of a vagina 232 or the vaginal wall 206 of the patient. In some other embodiments, the medical assembly 200 is configured to partially surround a portion of the vagina 232 of the patient.

In some embodiments, the ring shaped member 202 is structured in a manner such that it completely surrounds the vagina 232. In some embodiments, the ring shaped member 202 is configured to provide a support to the vagina 232 of the patient during an implantation procedure of a bodily implant (for example a mesh) into a pelvic region 240 of the patient. In some embodiments, the ring shaped member 202 is configured to support the bodily implant (for example a mesh) during the implantation procedure.

In some embodiments, the ring shaped member 202 is configured to be cut or released after implantation so that the ring shaped member 202 is transformed into a non-circular shape and thereby reducing the risk of constriction. The unneeded mesh can also be removed by cutting or releasing the mesh. An enlarged view of some mechanisms used to cut or release the ring shaped member 202 is shown in FIG. 3 and described later.

In some embodiments, the ring shaped member 202 is manufactured as a single component having a ring shape. In some embodiments, the ring shaped member 202 is manufactured as a multi component system, which is coupled to form the ring shaped member 202. The multi-component system may for example include two coupling portions—a first coupling portion 210 and a second coupling portion 212, in some embodiments, such that the first coupling portion 210 and the second coupling portion 212 are configured to be coupled together to form the ring shaped member 202. In some embodiments, the multi component system can include more than two coupling portions that are coupled to form the ring shaped member 202.

The ring shaped member 202 can be of a variety of different shapes, sizes, and configurations depending on the intended use of the medical assembly 200 and location of its placement within the body of the patient. The ring shaped member 202 can be shaped and sized to support the portion of the vagina 232 of the patient. In accordance with some embodiments, the ring shaped member 202 may be configured to conform to the shape of an organ or a tissue of the body of the patient. For example, the ring shaped member 202 may be placed in a ring shape, such as in the shape of a vaginal wall, to help it conform to the external contour of vagina 232 for easier fixation.

In some embodiments, the ring shaped member 202 can be made of a biodegradable material. In some embodiments, the biodegradable material can circumvent the need to cut the ring shaped member 102 as it would eventually be dissolved inside the body.

The ring shaped member 202 can be designed to have a coupling site 214. In some embodiments, the ring shaped member 202 has one coupling site 214. In other embodiments, the number of coupling sites can be more than one. The coupling site 214 is the portion of the ring shaped member 202 which is used for coupling the ring shaped member 202 to any other structure such as the arm member 204, as described below. FIG. 2A illustrates the ring shaped member 202 with two coupling sites—214a and 214b. However, there can be more coupling sites or even just a single coupling site, in various embodiments.

In some embodiments, the coupling site 214 can be designed to temporarily couple a structure to the ring shaped member 202. In other embodiments, the coupling site 214 can be designed to permanently couple the structure to the ring shaped member 202. In some embodiments, the structure that is coupled to the ring shaped member 202 can be the arm member 204.

The ring shaped member 202 is configured to hold the arm member 204 during implantation of the arm member 204 within the body. The ring shaped member 202 may provide a uniform grip and support to the arm member 204 thereby aiding in better fixation of the arm member 204 to bodily locations. The ring shaped member 202 is further configured to be cut after implantation so that the ring shaped member 202 is transformed into a non-circular shape and thereby reduces the risk of constriction.

In some embodiments, the arm member 204 is configured to be coupled to the ring shaped member 202 at the coupling site 214 and is configured to extend from the ring shaped member 202 to a bodily location upon placement. For example, the length of the arm member 204 can be provided to be configured to extend to the body location.

In some embodiments, the arm member 204 is removably or fixedly coupled to the ring shaped member 202. In some embodiments, the arm member is integrated to the ring shaped member 202 such that the ring shaped member 202 and the arm member 204 form a single integral structure. The arm member 204 may extend from any location of the ring shaped member 202.

In accordance with illustrated embodiments of FIGS. 2A and 2B, since the arm member 204 is coupled with the ring shaped member 202 at two of its portions, it is free to move with respect to the ring shaped member 202 and can take a defined shape based on an anatomical location. The defined shape can be any shape and can be modified based on the anatomical location of the patient where the ring shaped member 202 and the arm member 204 are attached.

A portion of the arm member 204 is configured to be coupled to the bodily location and provide a support to a vagina of a patient. For example, in an embodiment, a portion of the arm member 204 is configured to extend to a sacrum 208 of a patient. In some embodiments, the arm member 204 extends from the ring shaped member 202 to a location posterior to the vagina of the patient. In other embodiments, the arm member 204 extends from the ring shaped member 202 to a location anterior to the vagina of the patient. A view of the medical assembly 200 held to the outer surface of the vaginal wall 206 and extending to the sacrum 208 is illustrated in FIG. 2B.

In accordance with the illustrated embodiment of FIGS. 2A and 2B, the arm member 204 can contain one arm 216 referred to as a first arm 216 such that the first arm 216 is configured to extend from the ring shaped member 202 to a bodily location. In such cases, the arm member 204 can have a shape such as a U-shape.

Figure 2D:
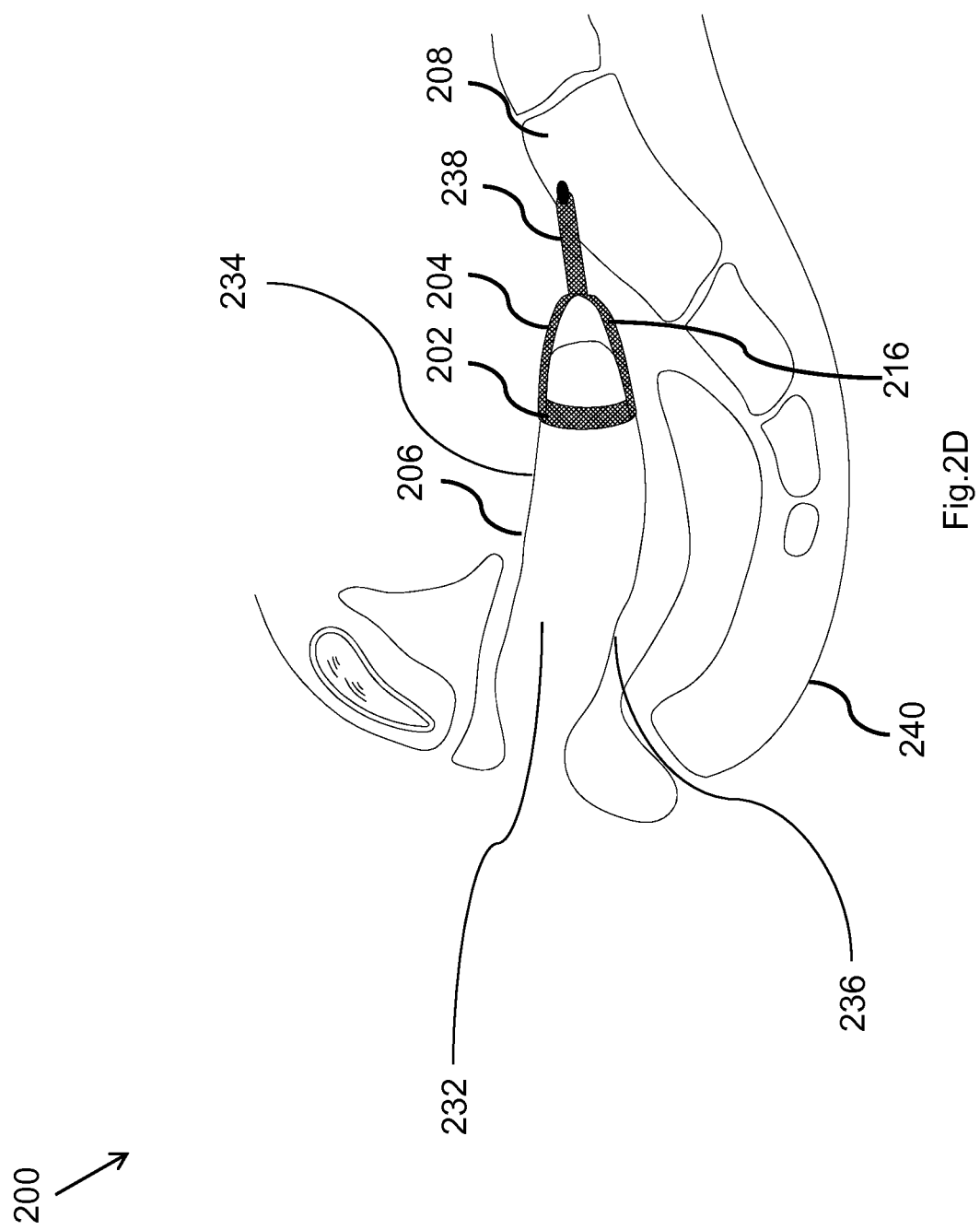
FIG. 2D is an illustration of placement of the medical device of FIG. 2C inside the body of the patient.
Figure 2E:
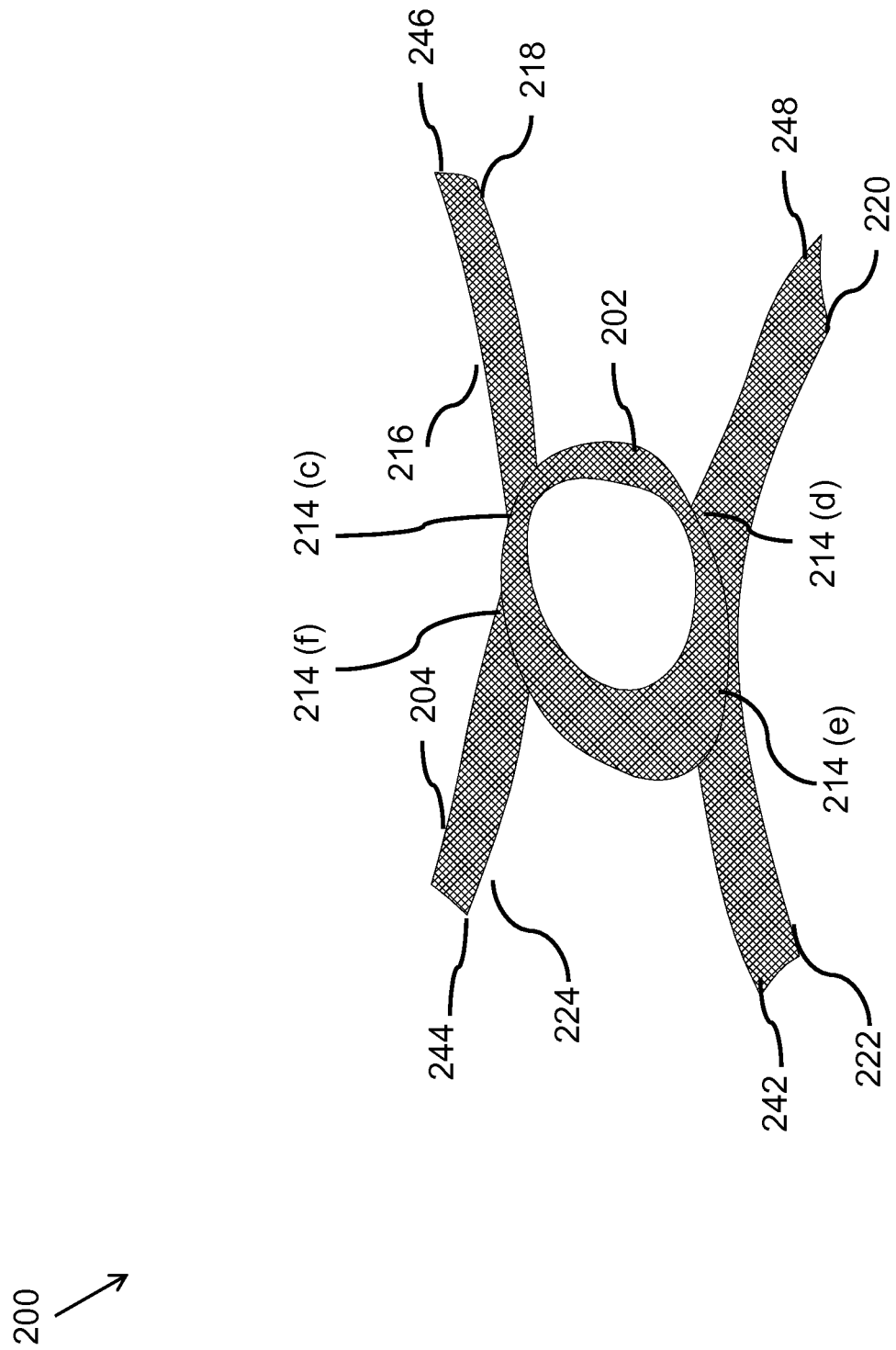
FIG. 2E is a perspective illustration of a medical assembly configured to be delivered into a patient's body for the treatment of a pelvic floor disorder.

In an example, the arm member 204 can have two arms—a first arm 246 and a second arm 238 such that the first arm 246 is configured to extend from the ring shaped member 202 and couple to the second arm 238 and the second arm 238 is configured to extend from the first arm 246 to a bodily location. In such cases, the arm member 204 can have a shape for example a yoke shape as shown in FIGS. 2C-2D. In some other embodiments, a third, fourth or even more arms can also be provided. An exemplary arm member 204 with such as four arms—248, 250, 242, and 244 is illustrated in FIG. 2E. As shown in FIG. 2E, the ring shaped member 202 can have four coupling sites 214 (*c*), 214 (*d*), 214 (*e*) and 214 (*f*).

The first arm 248 is coupled to the coupling site 214 (*c*) of the ring shaped member 202 and extends from the ring shaped member 202 to be coupled to a first portion 218 of the body of the patient. The second arm 250 is coupled to the coupling site 214 (*d*) of the ring shaped member 202 and extends from the ring shaped member 202 to be coupled to a second portion 220 of the body of the patient. The third arm 242 is coupled to the coupling site 214 (*e*) of the ring shaped member 202 and extends from the ring shaped member 202 to be coupled to a third portion 222 of the body of the patient. The fourth arm 244 is coupled to the coupling site 214 (*f*) of the ring shaped member 202 and extends from the ring shaped member 202 to be coupled to a forth portion 224 of the body of the patient.

The four different locations 218, 220, 222 and 224 for coupling the four arms on the ring shaped member 202 are spaced apart by a fixed distance. The fixed distance between the four different locations 218, 220, 222 and 224 may be altered in accordance with some embodiments of the medical assembly 200 and based on the intended site of the implantation. Further, the ring shaped member 202 disposed between the four arms may be structured in a manner such that it may completely surround the vagina. In some embodiments, the ring shaped member 202 surrounds the outer vaginal wall upon placement.

In an embodiment, the four arms can be placed between the outer wall of the vagina and the sacrum 208. In an exemplary embodiment, the first arm is attached to an anterior vaginal wall 234; the second arm is attached to a posterior vaginal wall, and the third arm and the fourth arm are attached to the sacrum 208 of the patient. The flexibility in the length of the arms 216, in some embodiments, may allow the medical assembly 200 to be disposed around any size of the vagina 232 in the body of the patient.

The ring shaped member 202 is disposed such that it substantially surrounds the complete outer vaginal wall 206 in the shape of a vaginal ring facilitating good contact with the anatomy to be supported. The ring shaped member 202 allows complementing the vagina 232 after the medical assembly is placed around the vagina 232. In some embodiments, the ring shaped member 202 can be manually adjusted into the desired position in the body of the patient during placement.

The bodily location can be a location posterior or anterior to the vagina 232 of the patient, the sacrum 208 or tissues proximate to the sacrum 208 or any other body location, in some embodiments. In some embodiments, the bodily location can be one of the bones or tissues at or proximate the back of the pelvis. In some embodiments, the bodily location can be a hip bone. In some embodiments, the bodily location can be a coccyx. In some embodiments, the bodily location can be a sacrospinous ligament or any other body location.

The shapes, sizes and configurations of the medical device 200 may vary based on the intended use and the site of the implantation. This has been described in conjunction with FIG. 1 in detail. The material of the arm member 204 and the ring shaped member 202 has also been described in conjunction with FIG. 1 in detail.

Figure 3B:
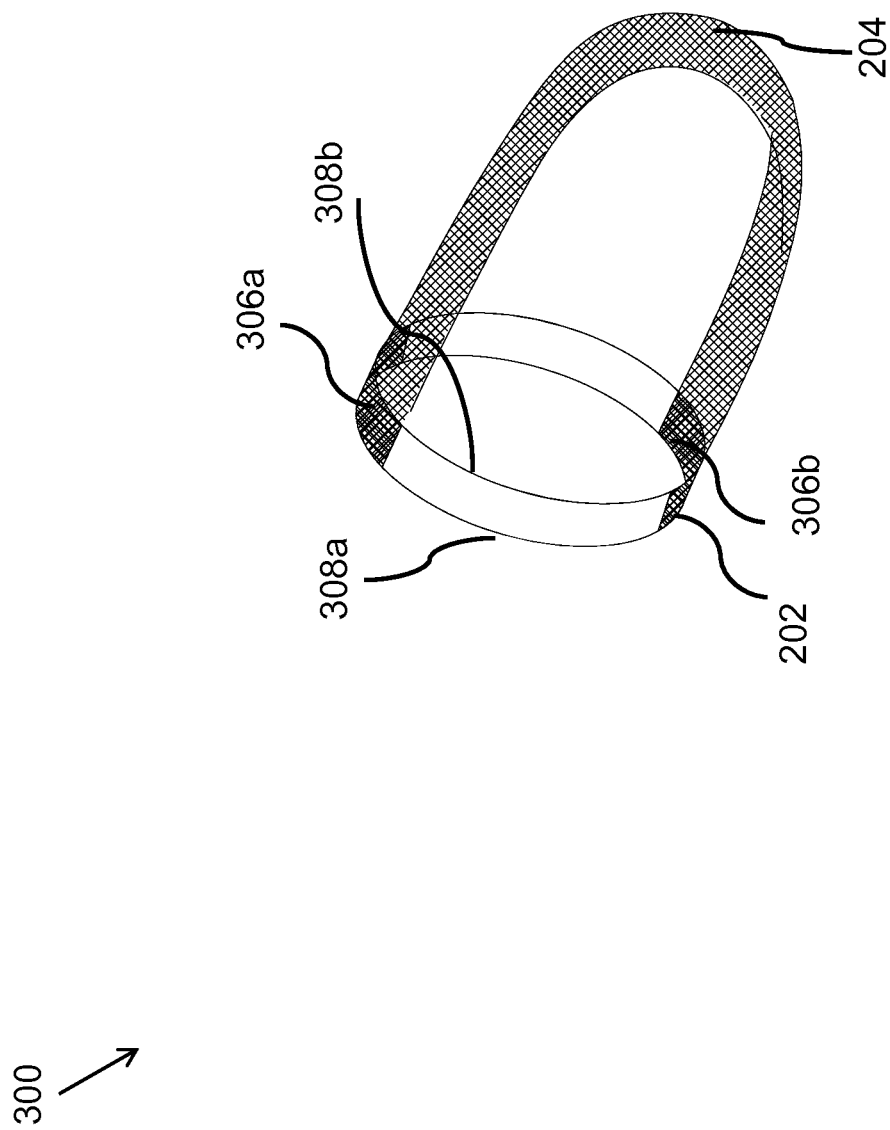
Figure 3C:
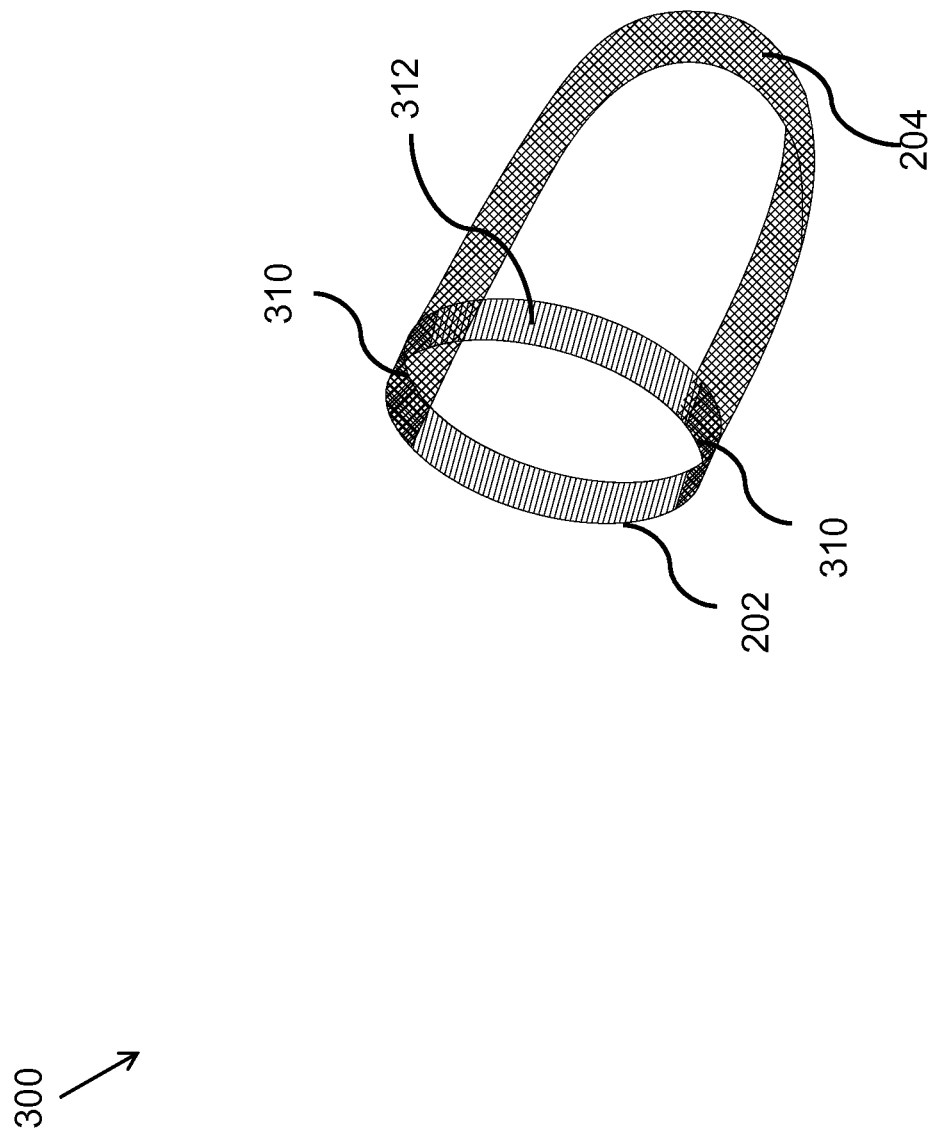

Referring to FIGS. 3A-3C in conjunction with FIGS. 2A-2E, an illustration of some features of the ring shaped member 202 are described.

In some embodiments, after implantation and fixation of the medical assembly 200, the ring shaped member 202 is transformed into a non-circular shape thereby reducing the risk of constriction. The unneeded mesh can also be removed by cutting or releasing the mesh as discussed. In an embodiment, as shown in FIG. 3A, after implantation and fixation of the medical assembly 200, the ring shaped member 202 may be cut along lines 302 and 304 as depicted in the figure. In some embodiments, the ring shaped member 202 may be cut at more than two locations along more than two lines such as to remove the unneeded mesh.

In some embodiments, (as shown in FIG. 3B) the ring shaped member 202 includes a mesh pad 306*a* and a mesh pad 306*b* (generally referred to as 306) held by a suture 308*a* and a suture 308*b* (generally referred to as 308). In some embodiments, the ring shaped member 202 can include only one mesh pad similar to the mesh pads 306. In some embodiments the mesh pad 306 can be held by a single suture similar to the sutures 308. In other embodiments, there can be even more than two sutures and/or mesh pads. The mesh pads 306 are held onto the vagina 232 or the outer vaginal wall 206 with the help of the sutures 308. The sutures 308 can be pulled away after fixation of the mesh pads 306 to the bodily location. In such cases, after pulling the sutures, there may not be any need of cutting the ring shaped member 202 since suture removal would mitigate the chance of vaginal constriction. In some embodiments of the invention, the sutures 308 are biodegradable in nature and can be left inside the body. In some embodiments, the mesh pads 306 can be biodegradable in nature.

In some embodiments, (as shown in FIG. 3C), the ring shaped member 202 is made of a hybrid of a permanent mesh 310 and a biodegradable mesh 312 In some embodiments, the portion of ring shaped member 202 with the permanent mesh 310 coupled to an arm member 204 (as discussed above in conjunction with FIG. 2). The portion with permanent mesh 310 is used for attachment to the bodily location (as illustrated in FIG. 3C). The remaining portion of the ring shaped member 202 is made of the biodegradable mesh 312. In some embodiments, the portion of the ring shaped member 202 having the biodegradable mesh 312 can degenerate or dissolve over a period of time such that the ring shaped member 202 would no more be a ring and therefore vaginal constriction can be prevented. In such cases, there may not be a need to cut the ring shaped member 202 after placement into the body. Additionally, in some embodiments, sutures or fasteners may be cut or removed to allow the ring shaped member 202 to transform in shape. In some embodiments, the sutures or fasteners maybe biodegradable. In other words, in some embodiments, the sutures or fasteners may dissolve over a period of time in the body to allow the ring shaped member to transform in size and/or shape.

In accordance with some embodiments of the invention, various cutting equipment or devices like scissors, knives etc. may be used to cut or remove at least a portion of the ring shaped member 202 after fixation of the medical assembly 200 to the bodily location.

Figure 4:
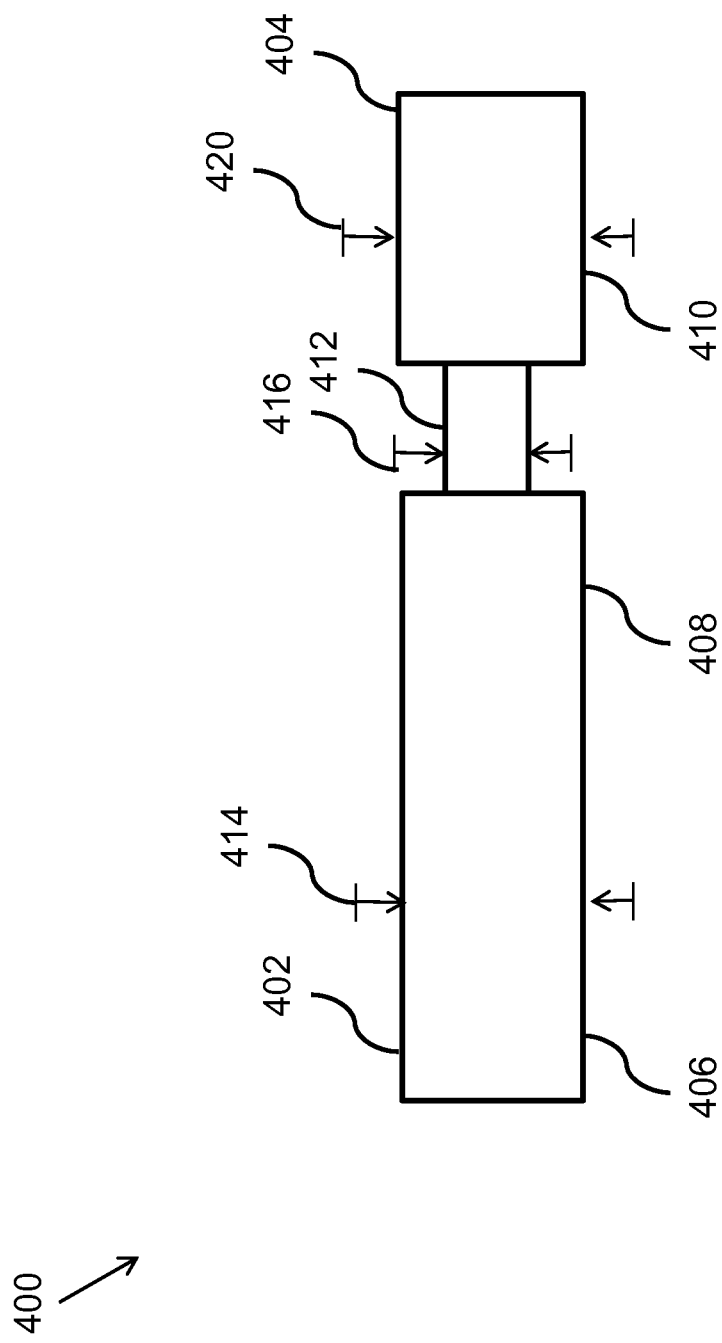
FIG. 4 is a schematic diagram of a medical device configured to be placed into a body of a patient to provide support to a medical assembly, in accordance with an embodiment of the present invention.

FIG. 4 illustrates a block diagram of a medical device 400, in accordance with an embodiment of the invention.

The medical device 400 includes an elongate portion 402 and a head portion 404 extending from the elongate portion 402.

The elongated portion 402 includes a proximal end portion 406 and a distal end portion 408. In some embodiments, the elongated portion 402 may have a predefined diameter referred to as a first diameter 414. In some embodiments, the elongated portion 402 can be a handle of the medical device 400 configured to be held by an operator external from a body tissue. In certain embodiments, the elongated portion 402 may be cylindrical in shape having a circular cross section at the distal end portion 408 and the proximal end portion 406. In other embodiments, the elongated portion 402 may be shaped such that the cross section is rectangular, or square, or of any other shape at its distal end portion 408 and the proximal end portion 402. Similarly, various other shapes of the elongated portion 402 are possible. For example, the cross section of the proximal end portion 406 and the distal end portion 408 can be pentagonal, hexagonal, octal, and the like. In accordance with some embodiments, the width of the elongated portion 402 is uniform or substantially uniform from the proximal end portion 406 to the distal end portion 408. However, in certain other embodiments, the elongated portion 402 may be tapered. In some embodiments, the elongated portion 402 is flexible in nature. In other embodiments, the elongated portion 402 is rigid. The head portion 404 extends from the distal end portion 408 of the elongate portion 402.

In some embodiments, the head portion 404 includes a tip portion 410 and a shoulder 412. In some embodiments, the shoulder 412 may have a predefined diameter referred to as a second diameter 416. The tip portion 510 defines a third diameter 420 at a location that has maximum diameter. In some embodiments, where the tip portion 410 has a varying diameter along its length, the third diameter 420 may be defined at a location that has maximum diameter of the tip portion 410.

In some embodiments, the first diameter 414 (of the elongated portion 402) is greater than the second diameter 416.

In some embodiments, the second diameter 416 is smaller than the first diameter 414 and the third diameter 420. In some embodiments, the first diameter 414 and the third diameter 420 may be equal. In some other embodiments, the first diameter 414 and the third diameter 420 may be different.

In some embodiments, the second diameter 416 is smaller than the first diameter 414 and the third diameter 420. In some embodiments, the first diameter 414 and the third diameter 420 may be equal. In some other embodiments, the first diameter 414 and the third diameter 420 may be different.

In some other embodiments, dimensions of the first diameter 414, the second diameter 416 and the third diameter 420 are substantially similar. In some embodiments, the surface of the head portion 404 is smooth.

In some embodiments, dimensions of the first diameter 414 and the second diameter 416 are less than the dimension of the third diameter 420. In some embodiments, the dimensions of the first diameter 414 and the second diameter 416 are constant. In some embodiments, the shoulder 412 of the head portion 404 has a T-end with an extendable feature. In some embodiments, the medical device 400 may have other geometry to position or hold the implant in place around the vagina.

In some embodiments of the invention, the medical device 400 includes multiple shoulders.

In some embodiments, the shoulder 412 is configured to hold an implant portion that is disposed around a vaginal wall through compress fit. In some embodiments, the implant portion can be medical assembly 200. In some embodiments, the surgeon/operator may use the shoulder of the head portion 404 to hold and fix the medical assembly 200 and place it around the vagina 232.

In some embodiments, the medical device 400 is a vaginal manipulator. In some embodiments, the medical device 400 is a paddle, dilator, stylet, or any other device. In some embodiments, the medical device 400 can be configured to facilitate holding or affixing a bodily implant (not shown) onto a bodily location. In some embodiments, the bodily implant can be similar to as described above in conjunction with FIG. 1 or FIGS. 2A-2E. The bodily implant may include the ring shaped member 202 and the arm member 204. This has been described in conjunction with FIGS. 2A-2E. In some embodiments, the medical device 400 may provide the vagina a shape thereby aiding the ring shaped member 202 to slide over the vagina. The medical device 400 can be configured to be placed so as to contact an inner wall of the vagina and the ring shaped member 202 of the bodily implant (for example the medical assembly 200) is placed on the outer wall 206 of the vagina 232 such that the ring shaped member 202 engages around the shoulder 412 and prevents the ring shaped member 202 from sliding off during implantation of the bodily implant.

In some embodiments, the medical device 400 indirectly engages with the bodily implant (for example with the medical assembly 200). As explained above, the medical assembly 200 can be placed on the outer wall 206 of the vagina 232 and the medical device 400 is inserted into the vagina 232 of the body of a patient. The medical device 400 provides a definite shape and stiffness to the vagina 232 from inside thereby providing the ring shaped member 202 of the medical assembly 200 a defined access and grip upon the outer wall 206 of the vagina 232. This indirect engagement facilities the process of placement of the bodily implant inside the body of a patient.

In some embodiments, a multiple piece or portion vaginal manipulator may be used. For example, a paddle, dilator, or stylet such as medical device 400 may be inserted into the vagina to provide shape the vagina. Then a lager member (not illustrated) such as a tubular member may be advanced or slid over the paddle, dilator, or stylet. The larger member may be configured to expand the vagina and functionally engage the implant to temporarily couple the implant to the vagina.

Figure 5A:
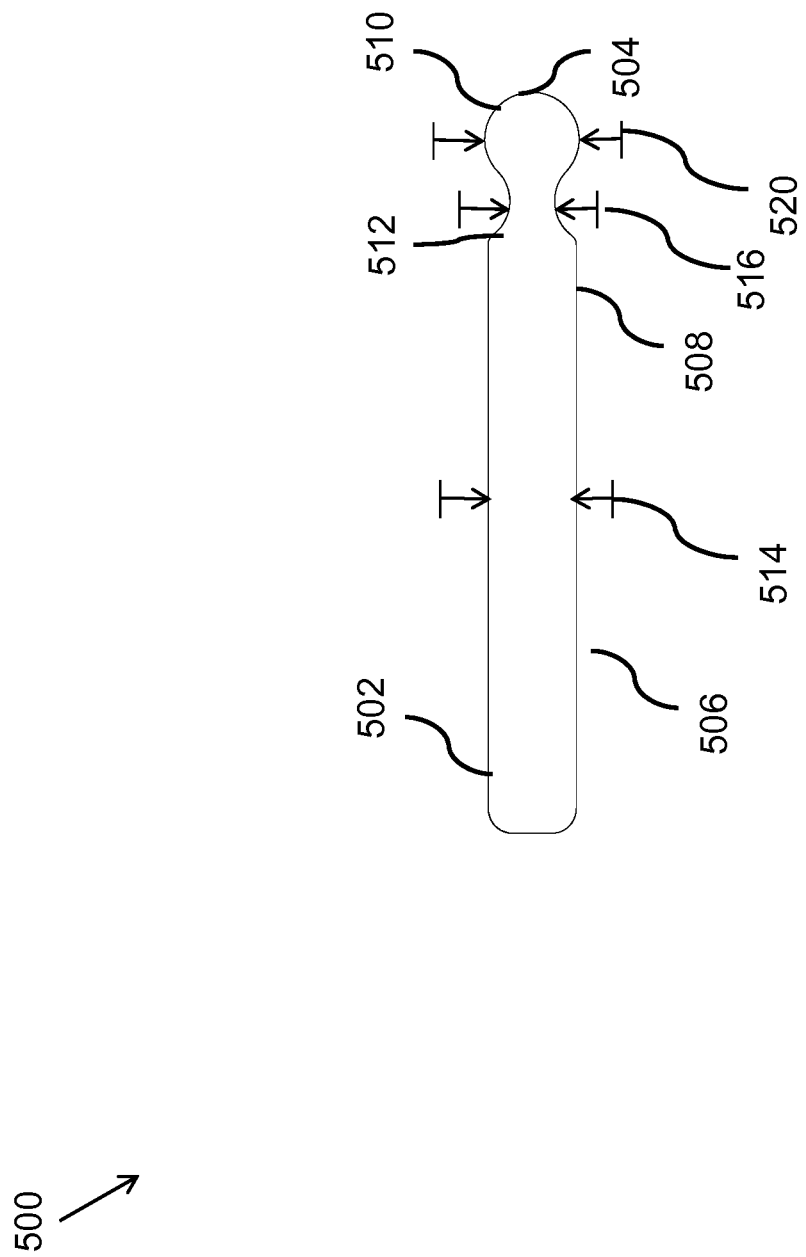
FIG. 5A illustrates a perspective view of a medical device configured to be placed into a body of a patient to provide support to a medical assembly, in accordance with some embodiments of the present invention.

FIG. 5A is a perspective view of a medical device 500, in accordance with an embodiment of the present invention. The medical device 500 includes an elongate member 502 and a head portion 504 extending from the elongated portion 502.

The elongated portion 502 includes a proximal end portion 506 and a distal end portion 508. In some embodiments, the elongated portion 502 may have a predefined diameter referred to as a first diameter 514. In some embodiments, the elongated portion 502 can be a handle of the medical device 500 configured to be held by an operator external from a body tissue. In certain embodiments, the elongated portion 502 may be cylindrical in shape having a circular cross section at the distal end portion 508 and the proximal end portion 506. In other embodiments, the elongated portion 502 may be shaped such that the cross section is rectangular, or square, or of any other shape at its distal end portion 508 and the proximal end portion 502. Similarly, various other shapes of the elongated portion 502 are possible. For example, the cross section of the proximal end portion 506 and the distal end portion 508 can be pentagonal, hexagonal, octal, and the like. In accordance with some embodiments, the width of the elongated portion 502 is uniform or substantially uniform from the proximal end portion 506 to the distal end portion 508 as illustrated in FIG. 5A. However, in certain other embodiments, the elongated portion 502 may be tapered. In some embodiments, the elongated portion 502 is flexible in nature. In other embodiments, the elongated portion 502 is rigid. The head portion 504 extends from the distal end portion 508 of the elongate portion 502.

In some embodiments, the head portion 504 includes a tip portion 510 and a shoulder 512. In some embodiments, the 504 shoulder may have a predefined diameter referred to as a second diameter 516. In some embodiments, as illustrated in FIG. 5A, the first diameter 514 (of the elongated portion 502) is greater than the second diameter 516. In accordance with the illustrated embodiments of FIG. 5A, the second diameter 516 is smaller than a third diameter 520 defined by the tip portion 510. In embodiments, where the tip portion 510 has a varying diameter along its length, the third diameter 520 may be defined at a location that has maximum diameter of the tip portion 510 such as shown in FIG. 5A.

In some embodiments, the shoulder 512 is configured to hold an implant portion that is disposed around a vaginal wall through compress fit. In some embodiments, the implant portion can be medical assembly 200. In some embodiments, the surgeon/operator may use the shoulder of the head portion 504 to hold and fix the medical assembly 200 and place it around the vagina 232.

In some embodiments, the second diameter 516 is smaller than the first diameter 514 and the third diameter 520 as shown in FIG. 5A. In some embodiments, the first diameter 514 and the third diameter 520 may be equal. In some other embodiments, the first diameter 514 and the third diameter 520 may be different.

Figure 5C:
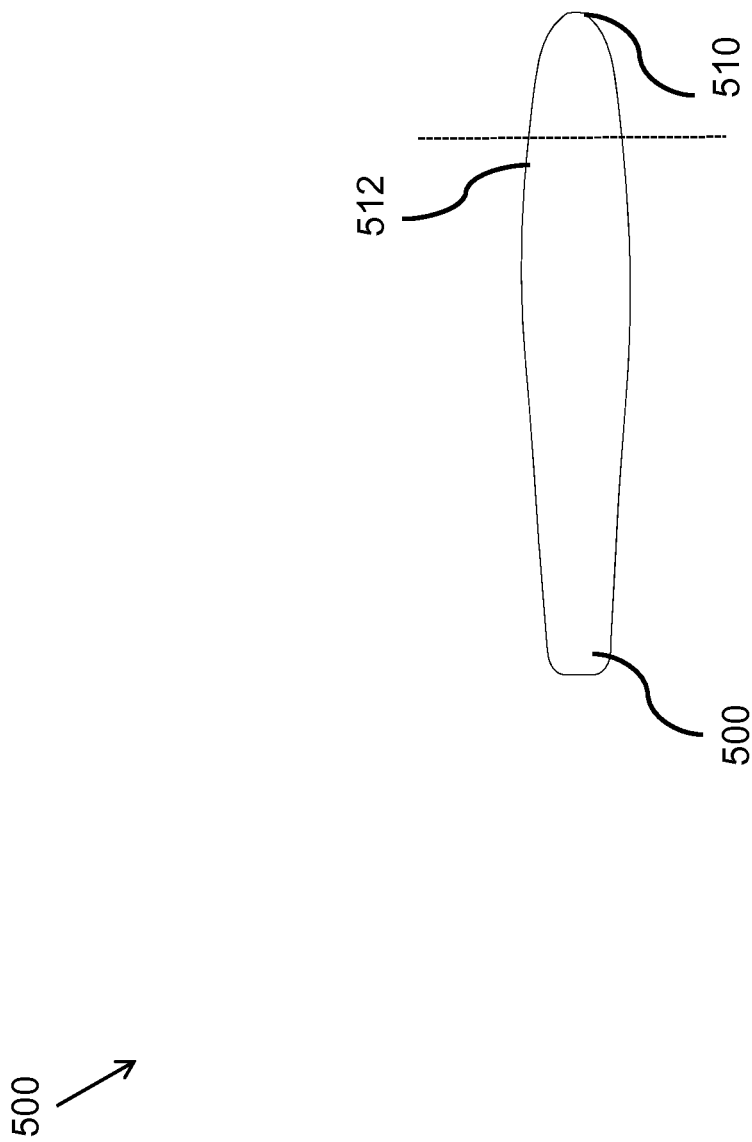
FIG. 5C illustrates a perspective view of a medical device configured to be placed into a body of a patient to provide support to a medical assembly.

In some embodiments, dimensions of the first diameter 514, the second diameter 516 and the third diameter 520 are substantially similar. In some embodiments, the surface of the head portion 504 is smooth as shown in FIG. 5C.

In some embodiments, the shoulder 512 of the head portion 504 can include an extendable feature at the tip portion 510. In some embodiments, the shoulder 512 of the head portion 504 can include an expandable or inflatable feature at the tip portion 510. The tip portion 510 may temporarily extend or expand or inflate to engage with bodily tissues or bodily implant and such as to prevent the ring shaped member 202 (as discussed below) from sliding off during implantation. The extendable or expandable or inflatable feature may allow for an ease in operation of the medical device 500 as it becomes easy to insert the device into the body of a patient and engage with the bodily tissues and the bodily implant. The extendable or expandable feature or the inflatable feature can for example be provided on the tip portion 510 of the medical device 500 depicted in FIG. 5C or FIG. 5F, or on the tip portion 510 of the medical device of the present invention in accordance with any other embodiment. In some embodiments, the extendable or expandable or the inflatable feature may be actuated through an actuator or some actuating mechanism that may be such as slidably or rotatably operated for actuation. The actuating mechanism may include such as a slider, a crank, a shaft, or any other mechanical linkage. In some embodiments, the expandable feature may includes a cage or a basket. In some embodiments, the inflatable feature may include a balloon member.

In some embodiments, dimensions of the first diameter 514 and the second diameter 516 are less than the dimension of the third diameter 520 as shown in FIG. 5E. In some embodiments, the dimensions of the first diameter 514 and the second diameter 516 can be the same. In some embodiments, the shoulder 512 of the head portion 504 has a T-end with an extendable feature. In some embodiments, the medical device 500 may have other geometry to position or hold the implant in place around the vagina.

In some embodiments, the medical device 500 is a vaginal manipulator. In other embodiments the medical device 500 is a paddle, dilator, stylet and the like. In some embodiments, the medical device 500 can be configured to facilitate holding or affixing the bodily implant 518 on an outer wall 206 of the vagina 232. In some embodiments, the bodily implant 518 can be similar to as described above in conjunction with FIG. 1 or FIGS. 2A-2E. The bodily implant 518 may include the ring shaped member 202 and the arm member 204. This has been described in conjunction with FIGS. 2A-2E. In some embodiments, the medical device 500 may provide the vagina a shape thereby aiding the ring shaped member 202 to slide over the vagina. The medical device 500 is placed inside the inner wall of the vagina and the ring shaped member 202 of the bodily implant (for example the medical assembly 200) is placed on the outer wall 206 of the vagina 232 such that the ring shaped member 202 engages around the shoulder 512 and prevents the ring shaped member 202 from sliding off during implantation as shown in FIGS. 5B, 5D, 5F and 5G.

Figure 5F:
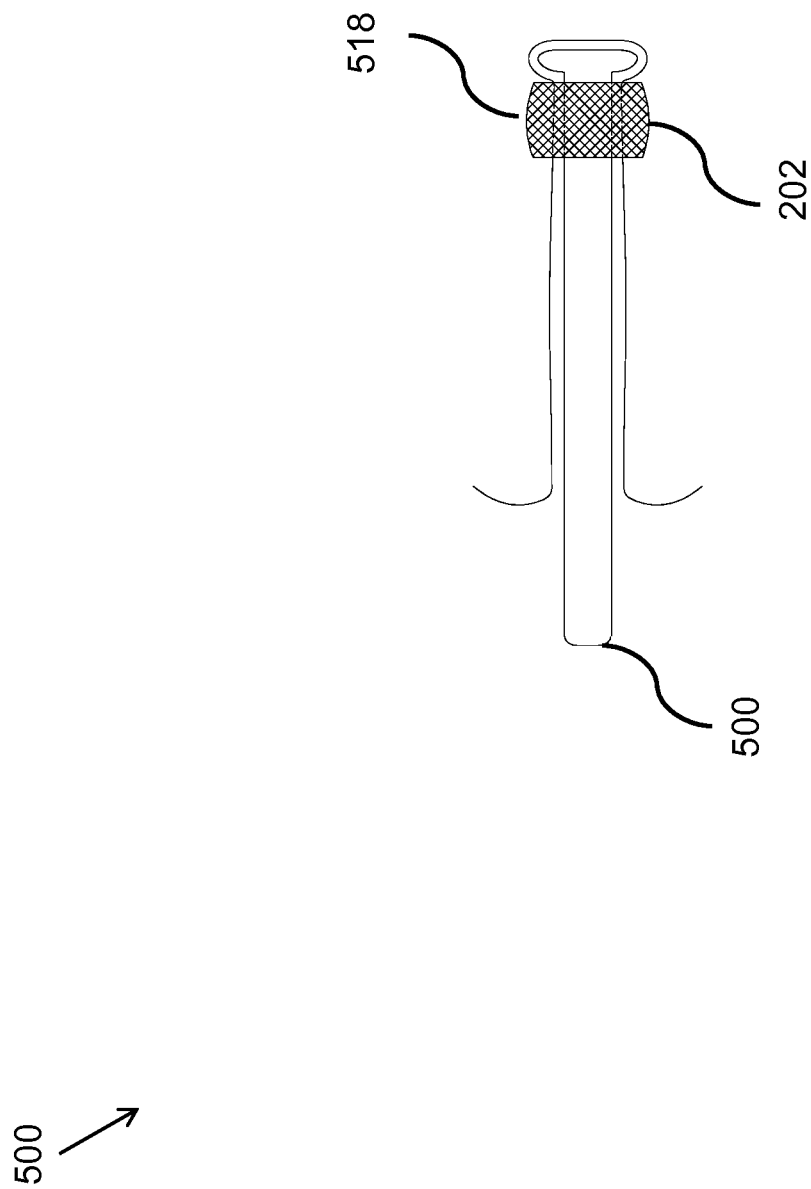
FIG. 5F illustrates a perspective view of the medical device of FIG. 5E being placed into the body of the patient to provide support to the medical assembly.

FIG. 5F illustrates perspective view of the medical device 500 being placed into a body of a patient to provide temporary support to the medical assembly 200 in accordance with T-shaped embodiments of the present invention.

Figure 5G:
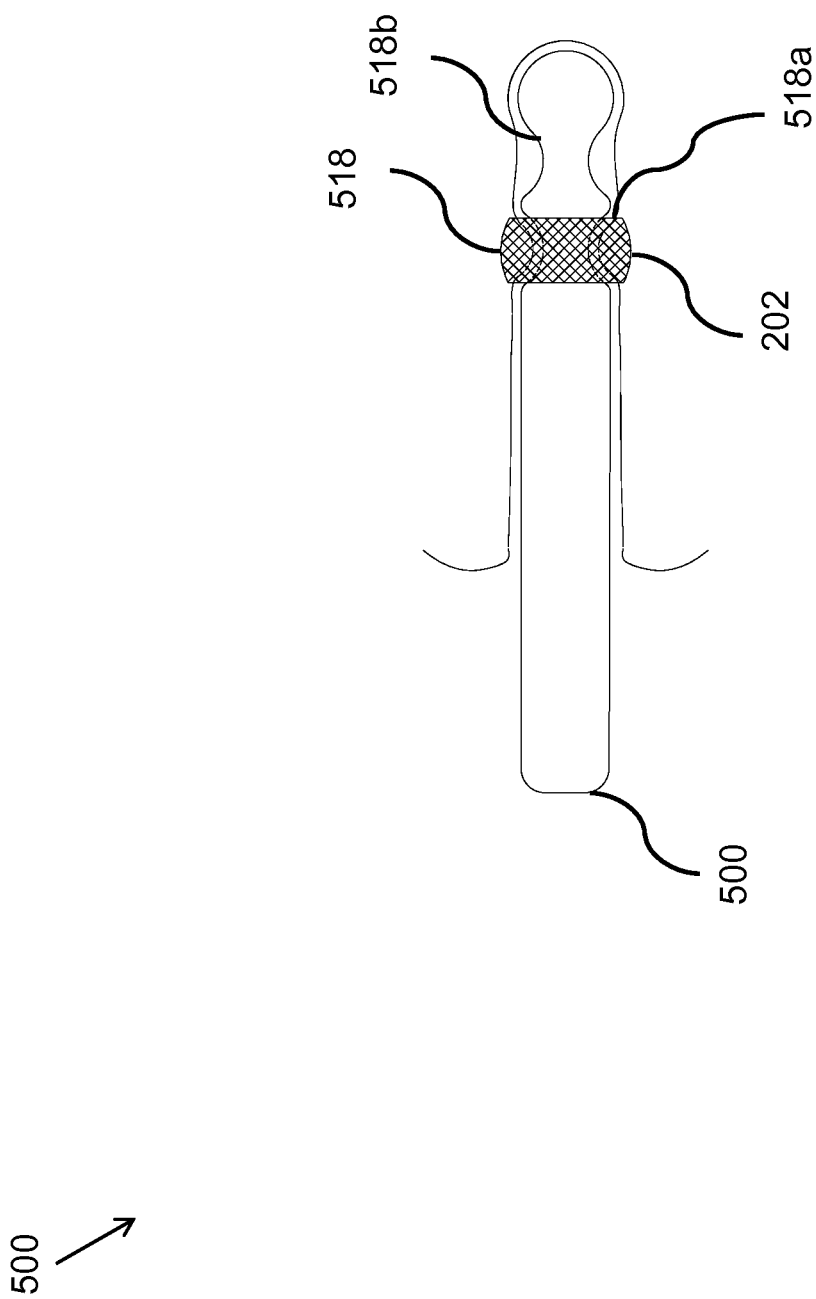
FIG. 5G illustrates a perspective view of a medical device being placed into a body of a patient to provide support to a medical assembly.

FIG. 5G illustrates perspective view of the medical device 500 being placed into a body of a patient to provide temporary support to the medical assembly 200, in accordance with multiple shoulder embodiments of the present invention. In accordance with some embodiments of the invention, the medical device 500 can have more than one shoulder such as the shoulder 512 to accommodate more than one ring shaped member similar to the ring shaped member 202 of the medical assembly 200 or multiple portions of the single ring shaped member 202. For example, in some embodiments, a first shoulder 518a may be configured to accommodate a first portion of the ring shaped member 202, and a second shoulder 518b may be configured to accommodate a second portion of the ring shaped member 202. In some embodiments, the plurality of shoulders helps facilitate the placement of the implant or ring shaped member at various locations along the vagina.

In some embodiments, the medical device 500 indirectly engages with the bodily implant 518 (for example with the medical assembly 200). As explained above, the medical assembly 200 is placed on the outer wall 206 of the vagina 232 and the medical device 500 is inserted into the vagina 232 of the body of a patient. The medical device 500 provides a definite shape and stiffness to the vagina 232 from inside thereby providing the ring shaped member 202 of the medical assembly 200 a defined access and grip upon the outer wall 206 of the vagina 232. This indirect engagement facilities the process of placement of the bodily implant 518 inside the body of a patient.

Figure 5H:
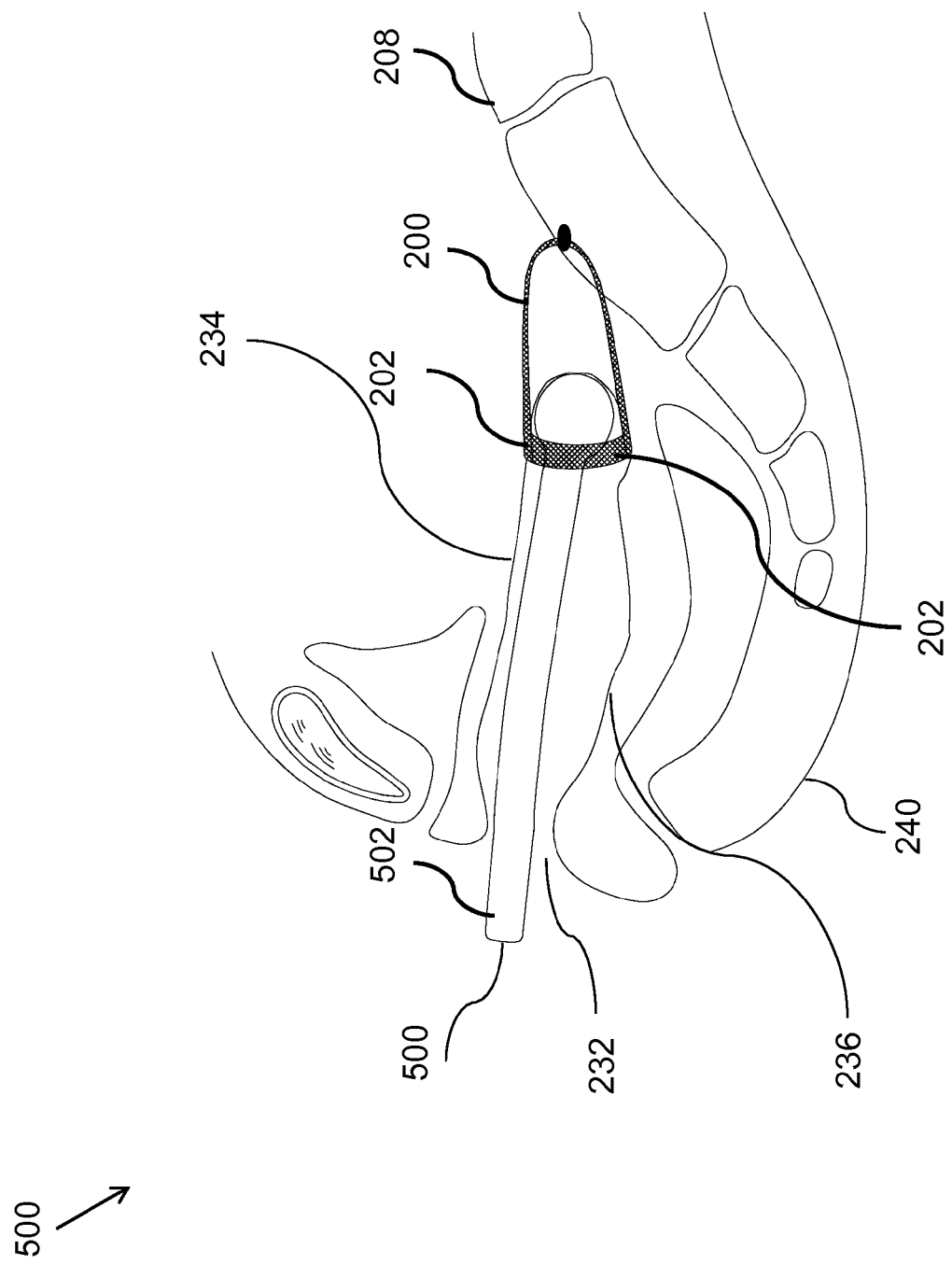
FIGS. 5H and 5I illustrate placement of a medical device within a body of a patient.

Referring to FIG. 5H in conjunction with FIGS. 2A-2B and FIGS. 5A-5G, engagement of the medical device 500 with the medical assembly 200 for placement of the medical assembly 200 inside the body of a patient is illustrated.

FIG. 5H illustrates placement of the medical device 500 within the body of a patient, in accordance with some embodiments of the present invention. The medical device 500 is used hereafter to describe the placement of the medical assembly 200. The body portions of the patient such as vaginal wall i.e. the anterior vaginal wall 234 and the posterior vaginal wall 236, the vagina 232, the sacrum 208, are also illustrated in FIG. 5H.

As shown, FIG. 5H illustrates the placement of the medical device 500 inside the vagina 232 for manipulation of the bodily tissues. As shown the tip portion 510 of the head portion 504 can be used to manipulate the tissues. The shoulder 512 assists in giving the vagina 232 a shape. Further the ring shaped member 202 as discussed above in medical assembly 200 is slid over the outer wall 206 of the vagina 232 as shown in FIG. 5H. The head portion 504 of the medical device 500 provides a definite shape to the vagina 232 to prevent the ring shaped member 202 from sliding off during attachment, thereby holding and fixing the ring shaped member 202 around the outer wall 206 of the vagina 232. The head portion 304 assists in moving the vagina 232 around so that it is easier to place the ring shaped member 202 and the arm member 204 coupled to the ring shaped member 202 into a patient's body.

As shown, the ring shaped member 202 is attached to outer wall 206 of the vagina 232. The first arm member 204 is attached to the vaginal wall i.e. the anterior vaginal wall 234 and the posterior vaginal wall 236 and is configured to extend from the ring shaped member 202 to the sacrum 208. FIG. 5H shows the placement of the medical assembly 200 with the single arm 204 that is configured to extend from the ring shaped member 202 to the sacrum 208 and form a U-shape.

Figure 5I:
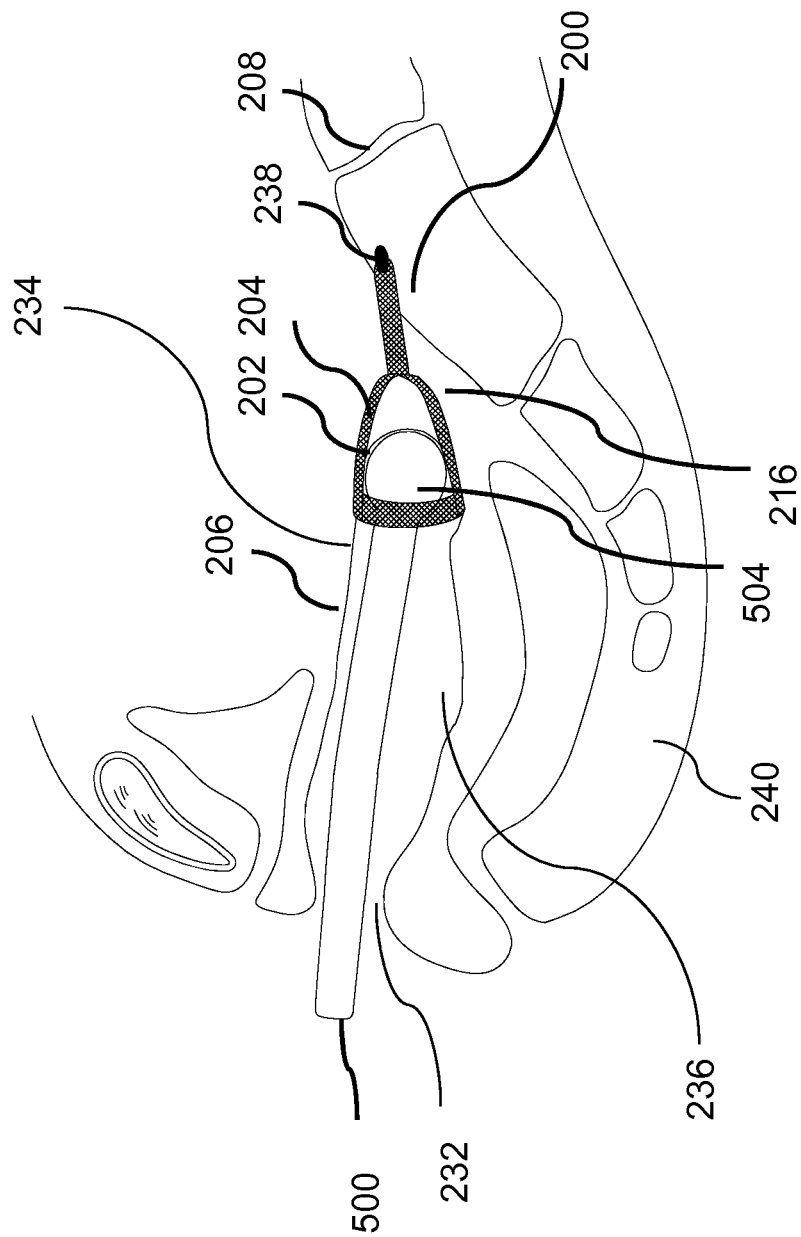

Referring to FIG. 5I in conjunction with FIGS. 2C-2D and FIGS. 5A-5G, placement of the medical device 500 and the medical assembly 200 is illustrated in accordance with the Y-shaped embodiment of the invention as described FIG. 2C. FIG. 5I shows the placement of the medical assembly 200 with the arm member 204 having two arms—the first arm 216 and the second arm 238.

As shown, the ring shaped member 202 is attached to the outer surface 206 vaginal wall. The first arm 216 is attached to the outer vaginal wall 206 i.e. the anterior vaginal wall 234 and the posterior vaginal wall 236 is configured to extend from the ring shaped member 202 and is coupled to the second arm 238. The second arm 238 is configured to extend from the first arm 216 to the sacrum 208 of the body of the patient as illustrated in FIG. 2D. The medical device 500 will provide support to vagina 232 while placement of medical assembly 200 as illustrated in FIG. 5I.

Figure 6:
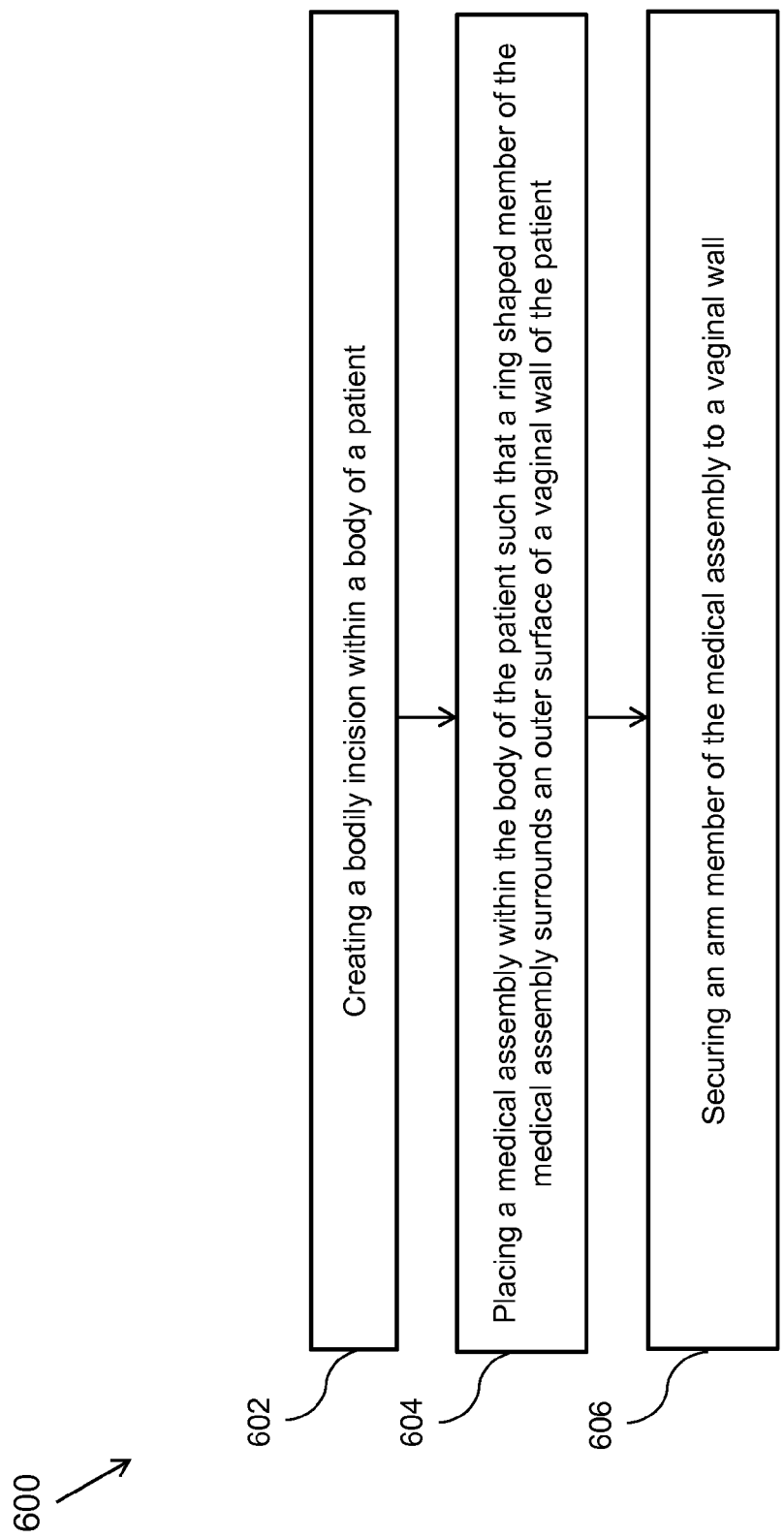
FIG. 6 illustrates a flowchart representing a method for placement of a medical assembly in a patient's body.

FIG. 6 is a flowchart illustrating a method of delivery and placement of the medical assembly 200 inside a body of a patient along with the use of the medical device 500.

Referring to FIG. 6 in conjunction with FIGS. 2A-2E and FIGS. 5A-5I, the method 600 of delivery and placement of the medical assembly 200 inside the body of the patient is described. As illustrated in FIG. 6, the method 600 includes creating a bodily incision in the body of the patient at step 602. The medical assembly 200 can be inserted within the body of the patient through the bodily incision. In some embodiments, the bodily incision is a vaginal incision. In other embodiments, the bodily incision is an abdominal incision. In still other embodiments, the bodily incision is a perennial incision made in a perennial body. The bodily incision can be made at various possible locations for facilitating the insertion of the medical assembly 200 within the patient's body.

The method 600 further includes placing the medical assembly 200 within the body of the patient at step 604 such that the ring shaped member 202 of the medical assembly 200 surrounds the outer surface of a vaginal wall of the patient. In some embodiments, the medical device 500 may be used to facilitate placement of the medical assembly 200. The medical device 500 gives the vagina 232 a shape thereby aiding the ring shaped member 202 to slide over the outer vaginal wall 206. The medical device 500 is placed inside the vagina 232 such that the ring shaped member 202 engages around the shoulder 512 and prevents the ring shaped member 202 from sliding off during implantation.

In embodiments, the ring shaped member 202 may be placed to completely surround the outer vaginal wall 206.

The method 600 further includes securing the arm member 204 of the medical assembly 200 at step 606.

The ring shaped member 202 is configured to temporarily hold a portion of the arm member 204 stationary with respect to a portion of the vagina 232 during the process of the securing at the step 606. In some embodiments, the arm member 204 extends from the ring shaped member 202 to a portion of the body of the patient to help retain the medical assembly 200 in place within the body of the patient. The ring shaped member 202 provides a uniform grip and support to the arm member 204 thereby aiding in better fixation of the arm member to bodily locations.

There can be various locations within the body of the patient where various arms of the arm member 204 may be coupled. In some embodiments, the bodily location is one of the bones at the back of the pelvis such as the sacrum and the like as shown in FIG. 2B. In other embodiments, the bodily location can be a hip bone. In some embodiments, the bodily location is a coccyx.

In some embodiments, the medical assembly 200, as described in accordance with various embodiments, may be tied with for example sutures, staples, adhesives, pins, tacks, and the like. In other embodiments, the pressure from the body tissues may provide enough support for fixing the arm member 204 with the body tissues.

The method 600 may also include cutting or releasing the ring shaped member 202. After implantation and fixation of the medical assembly 200, the ring shaped member 202 can be transformed into a non-circular shape by cutting the ring shaped member 202 and thereby reducing the risk of vaginal constriction.

The method 600 can also include adjusting tension of the arm member 204 for appropriate and desired treatment. For example, an appropriate tension may help in lifting disordered organs such as the anterior vaginal wall, posterior vaginal wall, cervix, and uterus as per the required treatment. An appropriate support is thus provided to the disordered organs by the medical assembly 200 or a portion of the medical assembly 200 such as the arm member 204.

In some embodiments, a medical assembly includes a ring shaped member configured to surround an organ of a patient; and an arm member coupled to the ring shaped member and configured to extend from the ring shaped member to a bodily location. The arm member is configured to be coupled to the bodily location and provide a support to the organ of the patient. The ring shaped member is configured to hold the arm member during implantation of the arm member within the body.

In some embodiments, the ring shaped member is further configured to change after implantation so that the ring shaped member is transformed into a non-circular shape. In some embodiments, the organ of the patient is a vagina. In some embodiments, the ring shaped member is made of a mesh material and is configured to be coupled to the organ. In some embodiments, the arm member includes a first arm. The first arm is configured to extend from the ring shaped member to a bodily location. In some embodiments, the arm member has a U shape. In some embodiments, the ring shaped member includes a biodegradable material. In some embodiments, the arm member includes a first arm configured to extend from the ring shaped member and couple to a second arm. The second arm is configured to extend from the first arm to a bodily location. In some embodiments, the arm member has a yoke shape.

In some embodiments, a medical device includes an elongate portion configured to be inserted into a vagina and a head portion. The elongate portion has a proximal end portion and a distal end portion. The head portion extends from the distal end portion of the elongate portion. The head portion includes a tip portion and a shoulder. The shoulder defines a diameter different than a diameter defined by the elongate portion and the tip portion such that the shoulder is configured to hold an implant portion disposed around a vaginal wall.

In some embodiments, the proximal portion of elongate member includes a handle. In some embodiments, the tip portion defines a substantially circular cross-section. In some embodiments, the shoulder is a first shoulder and the medical device further includes a second shoulder such that the second shoulder is configured to hold a second implant portion disposed around a vaginal wall. In some embodiments, the medical device is a vaginal manipulator. In some embodiments, the medical device is a dilator.

In some embodiments, a method includes placing a medical assembly within the body of the patient such that a ring shaped member of the medical assembly surrounds an outer surface of a vaginal wall of the patient; and securing an arm member of the medical assembly, the arm member extending from the ring shaped member to a body location, the arm member configured to support a vagina of the patient, wherein the ring shaped member is configured to hold the arm member stationary with respect to a portion of the vagina during securing.

In some embodiments, the method includes creating a bodily incision. The bodily incision may be used for delivering the medical assembly. In some embodiments, the method includes cutting a portion of the ring shaped member after securing the arm member to the vaginal wall. In some embodiments, the body location is a sacrum of the patient. In some embodiments, at least a portion of the medical assembly includes an implantable mesh. In some embodiments, the arm member includes one or more arms. In some embodiments, the arm member includes one of a yoke or a U-shape.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A medical assembly comprising:
   a ring shaped mesh member configured to surround an organ of a patient; and
   an arm mesh member including central portion, a first terminal end, and a second terminal end, the arm mesh member having a length extending between the first terminal end and the second terminal end, the central portion being located along the length between the first terminal end and the second terminal end, the first terminal end of the arm mesh member being coupled to a first portion of the ring shaped mesh member at a first coupling site, the second terminal end of the arm mesh member being coupled to a second portion of the ring shaped mesh member at a second coupling site, the first portion of the ring shaped mesh member at the first coupling site including a permanent mesh, the second portion of the ring shaped mesh member at the second coupling site including a permanent mesh, the ring shaped mesh member including a third portion disposed between the first portion and the second portion, the third portion including a biodegradable mesh, the first coupling site and the second coupling site being different locations on a circumference of the ring shaped mesh member,
   the central portion of the arm mesh member configured to extend to a bodily location, the arm mesh member configured to be coupled to the bodily location and provide a support to the organ of the patient,
   the biodegradable mesh of the third portion configured to degrade when the medical assembly is disposed within a body of the patient such that a circular shape of the ring shaped mesh member is transformed into a non-circular shape.

2. The medical assembly of claim 1, wherein the organ of the patient is a vagina.

3. The medical assembly of claim 1, wherein the first coupling site is separated from the second coupling site by a diameter of the ring shaped mesh member.

4. The medical assembly of claim 1, wherein all other portions besides the first portion of the ring shaped mesh member at the first coupling site and the second portion of the ring shaped mesh member at the second coupling site include the biodegradable mesh.

5. The medical assembly of claim 1, wherein the ring shaped mesh member includes a first end portion and a second end portion, the second end portion being coupled to the first end portion to form the circular shape of the ring shaped mesh member.

6. The medical assembly of claim 1, wherein the arm mesh member is a separate mesh construct from the ring shaped mesh member.

7. A method comprising:
   placing a medical assembly within a body of a patient such that a ring shaped mesh member of the medical assembly surrounds an outer surface of a vaginal wall of the patient, the ring shaped mesh member having a circular shape;
   securing an arm mesh member of the medical assembly to a sacrum of the patient, the arm mesh member including a central portion, a first terminal end, and a second terminal end, the arm mesh member having a length extending between the first terminal end and the second terminal end, the first terminal end of the arm mesh member being coupled to a first portion of the ring shaped mesh member at a first coupling site, the second terminal end of the arm mesh member being coupled to a second portion of the ring shaped mesh member at a second coupling site, the first portion of the ring shaped mesh member at the first coupling site including a permanent mesh, the second portion of the ring shaped mesh member at the second coupling site including a permanent mesh, the ring shaped mesh member including a third portion disposed between the first portion and the second portion, the third portion including a biodegradable mesh, the first coupling site and the second coupling site being different locations on a circumference of the ring shaped mesh member, the central portion of the arm mesh member extending from the ring shaped mesh member to the sacrum of the patient; and transforming the circular shape of the ring shaped mesh member into a non-circular shape in response to the biodegradable mesh of the third portion degrading within the body of the patient.

8. The method of claim 7, further comprising creating a bodily incision, the bodily incision used for delivering the medical assembly.

9. A medical assembly comprising:

a ring shaped mesh member configured to surround an organ of a patient, the ring shaped mesh member having a circular shape;

a first arm mesh member including a central portion, a first terminal end, and a second terminal end, the first arm mesh member having a length extending between the first terminal end and the second terminal end, the central portion being located along the length between the first terminal end and the second terminal end, the first terminal end of the first arm mesh member being coupled to a first portion of the ring shaped mesh member at a first coupling site, the second terminal end of the first arm mesh member being coupled to a second portion of the ring shaped mesh member at a second coupling site, the first portion of the ring shaped mesh member at the first coupling site including a permanent mesh, the second portion of the ring shaped mesh member at the second coupling site including a permanent mesh, the ring shaped mesh member including a third portion disposed between the first portion and the second portion, the third portion including a biodegradable mesh, the first coupling site and the second coupling site being different locations on a circumference of the ring shaped mesh member; and a second arm mesh member including a central portion, a first terminal end, and a second terminal end, the first terminal end of the second arm mesh member being coupled to the central region of the first arm mesh member, the second terminal end of the second arm mesh member being configured to extend to a bodily location, the biodegradable mesh of the third portion configured to degrade when the medical assembly is disposed within a body of the patient such that the circular shape of the ring shaped mesh member is transformed into a non-circular shape.

10. The medical assembly of claim 9, wherein the organ of the patient is a vagina.

* * * * *